(12) United States Patent
Park et al.

(10) Patent No.: US 11,850,134 B2
(45) Date of Patent: Dec. 26, 2023

(54) ABSORBENT ARTICLE

(71) Applicant: Kimberly-Clark Worldwide, Inc., Neenah, WI (US)

(72) Inventors: HaYeon Park, Seongnam-Si (KR); HyeJin Lee, Seoul-Si (KR); HanNa Park, Yongin-Si (KR)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 584 days.

(21) Appl. No.: 16/645,316

(22) PCT Filed: Sep. 29, 2017

(86) PCT No.: PCT/US2017/054355
§ 371 (c)(1),
(2) Date: Mar. 6, 2020

(87) PCT Pub. No.: WO2019/066907
PCT Pub. Date: Apr. 4, 2019

(65) Prior Publication Data
US 2020/0368081 A1    Nov. 26, 2020

(51) Int. Cl.
*A61F 13/535* (2006.01)
*A61F 13/47* (2006.01)
(Continued)

(52) U.S. Cl.
CPC ........ *A61F 13/535* (2013.01); *A61F 13/4704* (2013.01); *A61F 13/512* (2013.01);
(Continued)

(58) Field of Classification Search
CPC ............... A61F 13/535; A61F 13/4704; A61F 13/51104; A61F 13/512; A61F 13/5611; A61F 13/82
See application file for complete search history.

(56) References Cited

U.S. PATENT DOCUMENTS 2,408,508 A    10/1946  Canavan
3,115,877 A    12/1963  Harwood
(Continued)

FOREIGN PATENT DOCUMENTS

CN    1283981 A    2/2001
CN    1839775 A    10/2006
(Continued)

OTHER PUBLICATIONS

Pure Natural Health Care Private Limited, "Sanitary Napkins", http://www.purenaturalhealthcare.in/sanitary-napkins.html.
(Continued)

*Primary Examiner* — Jessica Arble
(74) *Attorney, Agent, or Firm* — KIMBERLY-CLARK WORLDWIDE, INC.

(57) ABSTRACT

An absorbent article can be configured to adhere to the body of a wearer in the area of the body of the wearer that may need bodily fluids absorbed. The absorbent article can be adhered to the body of the wearer to or around the vulva region of the body. The absorbent article can have an absorbent assembly which has a variable height in the longitudinal direction of the absorbent article.

18 Claims, 6 Drawing Sheets

(51) Int. Cl.
  *A61F 13/511* (2006.01)
  *A61F 13/512* (2006.01)
  *A61F 13/56* (2006.01)
  *A61F 13/82* (2006.01)

(52) U.S. Cl.
  CPC .... *A61F 13/51104* (2013.01); *A61F 13/5611* (2013.01); *A61F 13/82* (2013.01)

(56) References Cited

U.S. PATENT DOCUMENTS

| | | | |
|---|---|---|---|
| 4,804,380 A | 2/1989 | Lassen et al. | |
| 5,197,959 A | 3/1993 | Buell | |
| 5,545,156 A | 8/1996 | DiPalma et al. | |
| 5,599,337 A | 2/1997 | Mccoy | |
| 5,713,883 A * | 2/1998 | Hsieh | A61F 13/47263 604/385.01 |
| 6,171,291 B1 | 1/2001 | Osborn, III et al. | |
| 6,312,416 B1 * | 11/2001 | Brisebois | A61F 13/47218 604/385.01 |
| 6,486,379 B1 * | 11/2002 | Chen | A61F 13/5323 604/378 |
| 6,610,902 B1 | 8/2003 | Gustafsson et al. | |
| 6,632,210 B1 * | 10/2003 | Glasgow | A61F 13/82 604/385.03 |
| 6,695,827 B2 | 2/2004 | Chen et al. | |
| 6,703,538 B2 | 3/2004 | Lassen et al. | |
| 6,911,022 B2 | 6/2005 | Steger et al. | |
| 6,986,761 B1 | 1/2006 | Hines et al. | |
| 7,279,613 B2 | 10/2007 | Nozaki et al. | |
| 8,167,860 B1 | 5/2012 | Siegel | |
| 8,715,261 B2 | 5/2014 | Lira et al. | |
| 8,870,842 B2 | 10/2014 | Hill | |
| 8,961,486 B2 | 2/2015 | Stewart | |
| 9,017,304 B1 | 4/2015 | Betts | |
| 9,387,133 B2 | 7/2016 | Hooi | |
| 9,820,892 B2 | 11/2017 | Dennis et al. | |
| 2003/0093054 A1 | 5/2003 | Sierri et al. | |
| 2003/0097105 A1 | 5/2003 | Chen et al. | |
| 2004/0140048 A1 | 7/2004 | Lindsay et al. | |
| 2004/0147894 A1 | 7/2004 | Mizutani et al. | |
| 2005/0267434 A1 | 12/2005 | Tanio et al. | |
| 2005/0267435 A1 | 12/2005 | Tanio et al. | |
| 2006/0287635 A1 | 12/2006 | Angel | |
| 2007/0135788 A1 * | 6/2007 | Damay | A61F 13/4704 604/385.01 |
| 2007/0287973 A1 * | 12/2007 | Cohen | A61F 13/5611 604/385.03 |
| 2008/0300558 A1 | 12/2008 | Brusk et al. | |
| 2009/0118692 A1 | 5/2009 | Rosenfeld | |
| 2009/0204095 A1 * | 8/2009 | McDaniel | A61F 13/47227 604/387 |
| 2012/0215195 A1 * | 8/2012 | Lira | A61F 13/47227 604/385.03 |
| 2014/0230831 A1 | 8/2014 | Zaltsberg et al. | |

FOREIGN PATENT DOCUMENTS

| | | |
|---|---|---|
| CN | 104983516 A | 10/2015 |
| FR | 2682032 A1 | 4/1993 |
| GB | 2385526 B | 10/2005 |
| WO | 9629968 A1 | 10/1996 |

OTHER PUBLICATIONS

Lady Anion, "Sanitary Napkins", https://www.indiamart.com/proddetail/sanitary-napkins-14877393755.html.

* cited by examiner

ABSORBENT ARTICLE

BACKGROUND OF THE DISCLOSURE

Products such as absorbent articles are often used to collect and retain human body exudates containing, for example, urine, menses, and/or blood. Comfort, absorbency, and discretion are three main product attributes and areas of concern for the wearer of the absorbent article. In particular, a wearer is often interested in knowing that such products will absorb significant volumes of body exudates with minimal leakage in order to protect their undergarments, outer garments, or bedsheets from staining, and that such products will help them avoid the subsequent embarrassment brought on by such staining.

Currently, a wide variety of products for absorption of body exudates are available in the form of feminine pads, sanitary napkins, panty shields, and pantiliners. These products generally have an absorbent core positioned between a body-facing liquid permeable topsheet layer and a garment-facing liquid impermeable backsheet layer. The edges of the topsheet layer and the backsheet layer are often bonded together at their periphery to form a seal to contain the absorbent core and body exudates received into the product through the topsheet layer. In use, products such as, for example, feminine pads and sanitary napkins are typically positioned in the crotch portion of an undergarment for absorption of the body exudates and a garment attachment adhesive on the backsheet layer can be used to attach the product to the inner crotch portion of the undergarment. Some of these products can also include wing-like structures for wrapping about the wearer's undergarment to further secure the product to the undergarment and to protect the undergarment from staining. Such wing-like structures (also known as flaps or tabs) are frequently made from lateral extensions of the topsheet and/or backsheet layers.

Wearers of such absorbent articles, however, desire discretion, comfort, and close to the body fit. Conventional absorbent articles which are placed in the wearer's undergarment may not be able to provide such desired benefits to the wearer. Absorbent articles which are attached to a wearer's undergarment may experience twisting, contorting, and shifting out of place as they are subjected to the movement of the wearer's undergarment. Additionally, such conventional absorbent articles may have an overall length or shape which the wearer may feel is capable of being perceived by others through their clothing.

It has been suggested to use an adhesive to adhere an absorbent article directly to the skin of the wearer. The design of such absorbent articles is essentially the same as the absorbent articles which are attached to the inner crotch portion of the wearer's undergarment. But rather than utilizing a garment attachment adhesive, an adhesive can be applied to the body facing surface of the topsheet layer for attaching the absorbent article directly to the skin of the wearer. Alternatively, in another design, a portion of the backsheet layer is wrapped around and over the topsheet layer to partially define a body facing surface to which adhesive is applied for attaching the absorbent article directly to the skin of the wearer. While these designs are effective for adhering the absorbent article to the skin of the wearer, they are not comfortable for the wearer because the size and shape of the absorbent article is the same as those absorbent articles which are traditionally attached to the inner crotch region of the wearer's undergarment.

As a result, there remains a need for an absorbent article which is discrete during usage, easy to use, comfortable to wear, and inhibits leakage from the absorbent article.

SUMMARY OF THE DISCLOSURE

In various embodiments, an absorbent article can have a longitudinal direction and a transverse direction; an anterior region, a posterior region, and a central region positioned between the anterior region and the posterior region; a first transverse direction end edge and a second transverse direction end edge opposed to the first transverse direction end edge; a topsheet layer comprising a body facing surface; a backsheet layer; an absorbent system positioned between the topsheet layer and the backsheet layer, the absorbent system comprising an absorbent core and a perimeter edge; a depth direction wherein the absorbent system has a variable height in the depth direction in the longitudinal direction; a pair of lines of weakness in the posterior region which generally form a V-shape; and a body adhesive positioned on a portion of the body facing surface of the tospheet layer, the body adhesive comprising an interior perimeter separated by a spatial distance from the perimeter edge of the absorbent system.

In various embodiments, the pair of lines of weakness are formed by embossing lines.

In various embodiments, the height in the depth direction of the absorbent system in a portion of the anterior region of the absorbent article is greater than the height in the depth direction of the absorbent article in a portion of the posterior region of the absorbent article.

In various embodiments, the spatial distance separating the interior perimeter of the body adhesive from the perimeter edge of the absorbent system is from about 2 mm to about 10 mm.

In various embodiments, the spatial distance between the interior perimeter of the body adhesive and the perimeter edge of the absorbent system is uniform. In various embodiments, the spatial distance between the interior perimeter of the body adhesive and the perimeter edge of the absorbent system is non-uniform.

In various embodiments, a portion of the posterior region of the absorbent article is free from body adhesive.

In various embodiments, the absorbent article can further have a distribution layer. In various embodiments, the distribution layer has a length in the longitudinal direction which is longer than a length in the longitudinal direction of the absorbent core.

In various embodiments, the absorbent article can further have a notch extending from a perimeter edge of the absorbent article an in a direction towards the longitudinal axis of the absorbent article. In various embodiments, the notch is located in the posterior region of the absorbent article. In various embodiments, the absorbent article can further have a second notch extending from a perimeter edge of the absorbent article and in a direction towards the longitudinal axis of the absorbent article in the anterior region of the absorbent article.

In various embodiments, the absorbent article can have a secondary topsheet.

In various embodiments, the absorbent article can have a third line of weakness extending along a portion of a longitudinal axis in the posterior region of the absorbent article. In various embodiments, the absorbent article can have a second pair of lines of weakness in the anterior region of the absorbent article which generally form a V-shape.

In various embodiments, the absorbent article can further have a fluid intake layer. In various embodiments, the fluid intake layer has an opening.

Figure 1A:
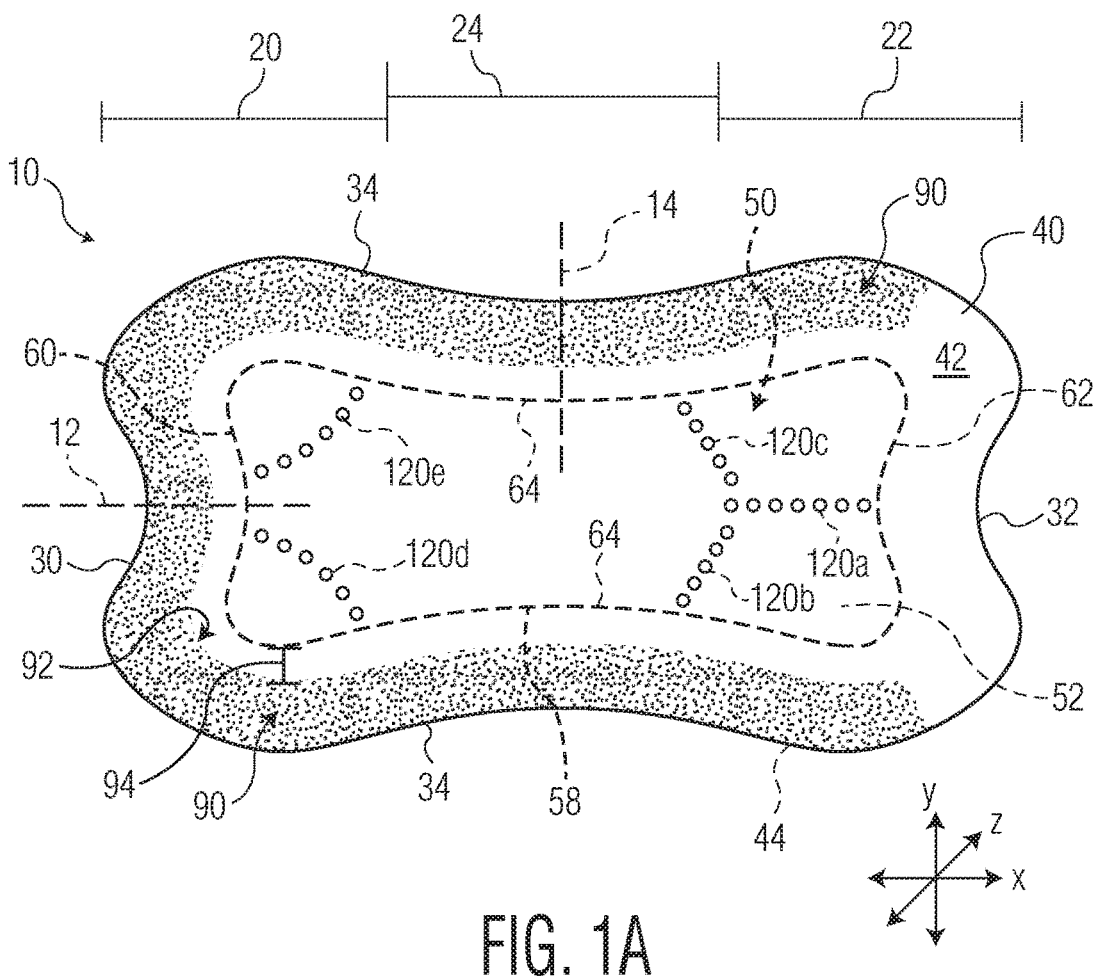
FIG. 1A is a top view of an exemplary embodiment of an absorbent article.

Repeat use of reference characters in the present specification and drawings is intended to represent the same or analogous features or elements of the disclosure.

DETAILED DESCRIPTION OF THE DISCLOSURE

The present disclosure is directed towards an absorbent article configured to adhere to the body of a wearer in the area of the body of the wearer that may need bodily fluids absorbed. In various embodiments, the absorbent article is adhered to the body of the wearer to or around the vulva region of the body. By "to or around the vulva region", it is meant adjacent regions of the body of a female including the pubic region and the perinea region. When applied to or around the vulva region of the female body, the absorbent article may be used as a panty-liner, sanitary napkin, or incontinence article. Additionally, the absorbent article may be worn as an underwear substitute as the absorbent article of the present disclosure does not need underwear to hold the absorbent article in place. As an underwear substitute, the absorbent article provides protection to the vulva region by creating a barrier between the outer clothing of the wearer and the vulva of the wearer. When worn as an underwear substitute, the absorbent article can serve to protect the outer clothing of the wearer from bodily discharges from the vulva region of the wearer's body. In addition, when the absorbent article is worn as an underwear substitute, the absorbent article also serves to protect the sensitive skin and body features of the vulva region from roughness of the outer clothing, thereby preventing or alleviating irritation to the sensitive skin and body features of the vulva region.

Definitions

As used herein, the term "absorbent article" refers herein to an article which may be placed against the body of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, feminine hygiene products including, but not limited to, menstrual pads, sanitary napkins, feminine pads, pantiliners, and panty shields, and incontinence products, and the like without departing from the scope of the present disclosure.

As used herein, the term "airlaid" refers herein to a web manufactured by an airlaying process In the airlaying process, bundles of small fibers having typical lengths ranging from about 3 to about 52 mm are separated and entrained in an air supply and then deposited onto a forming screen, usually with the assistance of a vacuum supply. The randomly deposited fibers are then bonded to one another using, for example, hot air to activate a binder component or a latex adhesive. Airlaying is taught in, for example, U.S. Pat. No. 4,640,810 to Laursen, et al., which is incorporated herein in its entirety by reference thereto for all purposes.

As used herein, the term "bonded" refers to the joining, adhering, connecting, attaching, or the like, of two elements. Two elements will be considered bonded together when they are joined, adhered, connected, attached, or the like, directly to one another or indirectly to one another, such as when bonded to an intermediate element. The bonding can occur via, for example, adhesive, pressure bonding, thermal bonding, ultrasonic bonding, stitching, suturing, and/or welding.

As used herein, the term "bonded carded web" refers herein to webs that are made from staple fibers which are sent through a combing or carding unit which separates or breaks apart and aligns the staple fibers in the machine direction to form a generally machine direction oriented fibrous nonwoven web. This material may be bonded together by methods that can include point bonding, through air bonding, ultrasonic bonding, adhesive bonding, etc.

As used herein, the term "coform" refers herein to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff, and also superabsorbent particles, inorganic and/or organic absorbent materials, treated polymeric staple fibers and so forth. Some examples of such coform materials are disclosed in U.S. Pat. No. 4,100,324 to Anderson, et al., U.S. Pat. No. 4,818,464 to Lau, U.S. Pat. No. 5,284,703 to Everhart, et al., and U.S. Pat. No. 5,350,624 to Georger, et al., each of which are incorporated herein in their entirety by reference thereto for all purposes.

As used herein, the term "conjugate fibers" refers herein to fibers which have been formed from at least two polymer sources extruded from separate extruders and spun together to form on fiber. Conjugate fibers are also sometimes referred to as bicomponent or multicomponent fibers. The polymers are arranged in substantially constantly positioned distinct zones across the cross-sections of the conjugate fibers and extend continuously along the length of the conjugate fibers. The configuration of such a conjugate fiber may be, for example, a sheath/core arrangement where one polymer is surrounded by another, or may be a side-by-side arrangement, a pie arrangement, or an "islands-in-the-sea"

arrangement. Conjugate fibers are taught by U.S. Pat. No. 5,108,820 to Kaneko, et al., U.S. Pat. No. 4,795,668 to Krueger, et al., U.S. Pat. No. 5,540,992 to Marcher, et al., U.S. Pat. No. 5,336,552 to Strack, et al., U.S. Pat. No. 5,425,987 to Shawver, and U.S. Pat. No. 5,382,400 to Pike, et al., each being incorporated herein in their entirety by reference thereto for all purposes. For two component fibers, the polymers may be present in ratios of 75/25, 50/50, 25/75 or any other desired ratio. Additionally, polymer additives such as processing aids may be included in each zone.

As used herein, the term "machine direction" (MD) refers to the length of a fabric in the direction in which it is produced, as opposed to a "cross-machine direction" (CD) which refers to the width of a fabric in a direction generally perpendicular to the machine direction.

As used herein, the term "meltblown web" refers herein to a nonwoven web that is formed by a process in which a molten thermoplastic material is extruded through a plurality of fine, usually circular, die capillaries as molten fibers into converging high velocity gas (e.g., air) streams that attenuate the fibers of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buten, et al., which is incorporated herein in its entirety by reference thereto for all purposes. Generally speaking, meltblown fibers may be microfibers that are substantially continuous or discontinuous, generally smaller than 10 microns in diameter, and generally tacky when deposited onto a collecting surface.

As used herein, the term "nonwoven fabric" or "nonwoven web" refers herein to a web having a structure of individual fibers or threads which are interlaid, but not in an identifiable manner as in a knitted fabric. Nonwoven fabrics or webs have been formed from many processes such as, for example, meltblowing processes, spunbonding processes, through-air bonded carded web (also known as BCW and TABCW) processes, etc. The basis weight of nonwoven webs may generally vary, such as, from about 5, 10, or 20 gsm to about 120, 125, or 150 gsm.

As used herein, the term "spunbond web" refers herein to a web containing small diameter substantially continuous fibers. The fibers are formed by extruding a molten thermoplastic material from a plurality of fine, usually circular, capillaries of a spinneret with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki, et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in their entirety by reference thereto for all purposes. Spunbond fibers are generally not tacky when they are deposited onto a collecting surface. Spunbond fibers may sometimes have diameters less than about 40 microns, and often between about 5 to about 20 microns.

As used herein, the terms "superabsorbent polymer," "superabsorbent," or "SAP" shall be used interchangeably and shall refer to polymers that can absorb and retain extremely large amounts of a liquid relative to their own mass. Water absorbing polymers, which are classified as hydrogels, which can be cross-linked, absorb aqueous solutions through hydrogen bonding and other polar forces with water molecules. A SAP's ability to absorb water is based in par on iconicity (a factor of the ionic concentration of the aqueous solution), and the SAP functional polar groups that have an affinity for water. SAP are typically made from the polymerization of acrylic acid blended with sodium hydroxide I the presence of an initiator to form a poly-acrylic acid sodium salt (sometimes referred to as sodium polyacrylate). Other materials are also used to make a superabsorbent polymer, such as polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile. SAP may be present in absorbent articles in particle or fibrous form or as a coating or another material or fiber.

Absorbent Article:

The present disclosure is directed towards an absorbent article configured to adhere to the body of a wearer in the area of the body of the wearer that may need bodily fluids absorbed. In various embodiments, the absorbent article is adhered to the body of the wearer to or around the vulva region of the body. The absorbent article can be of a size and shape to fit in the vulva region and possibly the surrounding pubic region and perinea regions of the female torso. In addition to contacting the skin of the vulva, pubic and perinea regions of the wearer, the absorbent article may also contact and adhere to any hair present in the vulva area of the wearer which may be present.

To gain a better understanding of the vulva region and surrounding regions of the female body, a general description of the anatomical structures can be found in *The Illustrated Running Press Edition of the American Classic Gray's Anatomy* (1974) by Henry Gray and Structure and Function in Man (1974) by Stanley W. Jacob, M.D., F.A.C.S. and relevant portions are included herein by reference. The general form can be found in *Anatomy for an Artist: Elements of Form* by Eliot Goldfinger and relevant portions are included herein by reference. The general description of the pubic hair covering these regions can be found in *Woman's Body: A Manual for Life* and relevant portions are included herein by reference.

The female anatomical structures to be described include the leg and the lower torso. The external anatomical structures of the lower torso include the gluteal region and the perineum region. The gluteal region includes the buttocks and the anus. The anatomical structure involved on the leg is the medial surface of the upper thigh.

The gluteal region includes generally the buttocks and anus and is typically bound in front by the line of the buttocks and the gluteal folds, in the back by the sacral triangle, and the sides by lines extending through the greater trochanters. The shape of the gluteal region is roughly hemi-spherical and convex, and is determined by a series of muscles including the gluteus maximus and a series of fat pads including the posterior gluteal fat pad. The line of the buttocks separates the gluteal region and the perineum region.

The upper thigh region includes typically the right and left thigh and is typically bound on top by the thigh lines and the sides by the front and back of the leg. The thigh lines are two lines that are on either side of the labia and each of the lines runs along the line of the inguinal ligament to the gluteal folds and marks where the upper thigh meets the lower torso. The shape of the region is roughly a portion of a tapered cylinder and convex, and is shaped by a series of muscle groups including the gracilis, pectineus, adductor longus, adductor brevis, and adductor magnus and series of fat pads including the inner thigh fat pad.

The perineum region, which extends from the inferior outlet of the pelvis to the bony structure of the coccyx, is comprised of two divisions, the urogenital triangle and the anal division or obstetrical perineum. The region includes the external organs of reproduction: the mons pubis, labia majora and minora, clitoris, meatus urinarius, and the opening to the vagina. The region is generally bound in front by the lower abdominal line, on the sides the thigh lines, and in the back the line of the buttocks. The abdominal line is a line that passes across the top of the pubis. The lines of the buttocks are lines that connect the thigh lines to the gluteal cleft. For convenience in describing the form and created spaces in the perineum region, this region will be subdivided into three regions—an anterior region including the mons pubis, a central region including the labia majora and minora, and posterior region. The anterior region is bound in front by the lower abdominal line, in back by anterior commissure, and on the sides by line of the labia. The central region is bound in front by the anterior commissure, in the back by the posterior commissure, and on the side by the line of the labia. The posterior region is bound in front by the line of the labia, in the back by the lines of the buttocks, and on the sides the thigh line.

The vulva region (or vaginal region) includes the female external genitalia and generally includes the anterior and central regions of the perineum. The mons pubis (or veneris) is generally a rounded eminence in front of the symphysis pubis, formed by a collection of fatty tissue including the pubic fat pad beneath the integument and is generally covered with pubic hair. The labia majora are generally two prominent longitudinal cutaneous folds extending downward from the mons veneris to the anterior boundary of the perineum, and generally enclosing the common urinary-sexual opening. The space between the two folds is the labial cleft. Each labium has generally two surfaces, an outer, which is pigmented and covered generally with strong, crisp pubic hairs, and an inner within the labia cleft, which is smooth and is beset with large sebaceous follicles and is continuous with the genito-urinary mucous tract; between the two there is considerable quantity of areolar tissue, fat including the labia fat pad, and tissue besides vessels, meeting the anterior commissure. Posteriorly they are typically not joined, but generally appear to become lost in the neighboring integument, terminating close to, and nearly parallel with each other. Together with the connecting skin between them, they form the posterior commissure or posterior boundary of the vulval orifice. The interval between the posterior commissure and the anus constitutes the perineum region. The fourchette is the anterior edge of the perineum, and between it and the hymen is a depression, the fossa navicularis. The line of the labia separates the labia and the perineum region.

The labia minora are two small cutaneous folds, situated generally within the labia majora, and extending from the clitoris obliquely downward, outward, and backward on each side of the orifice of the vagina.

The form of the perineum, gluteal, and upper thigh regions combine to form a very intricate skin topography and spaces. The roughly two-hemispherical-like forms of the buttocks, the roughly tapered-cylinder-like form of the upper thigh, split-teardrop-like form of the vulvar region create intricate generally convex topography with intersections to form a series of recesses. The generally convex topography of the buttocks, the vulvar region, and upper thigh join to create spaces including two inner thigh grooves along two thigh lines, a depression in the posterior perineum region and a cleft extending through the labia and gluteal clefts. The grooves, depression, and cleft are like interconnected recesses in the topography. The central region generally has lateral sides separated by a distal surface created by the labial cleft and includes the labial cleft.

Pubic hair generally cover some of these regions and fill in a portion of these recesses especially the labial cleft and the portion of the groove of the thigh parallel to the labial cleft to create a hair surface topography. The hair topography is the surface topography of an imaginary distal surface created by the hair. The depression of the perineum, thigh groove parallel to the gluteal cleft, and the gluteal cleft generally has little or no pubic hair. The skin topography combines with the hair topography to create an overall body topography.

This intricate space created by the intricate body form in this region of the body varies between women in both size and form, and varies with the position and movement of the women. Some of these variations are summarized in "Female genital appearance: 'normality' unfolds" by Jillian Lloyd et al., BJOG: An International Journal of Obstetrics and Gynecology, May 2005, Vol. 112, pp. 643-646 and is included herein by reference.

Figure 1B:
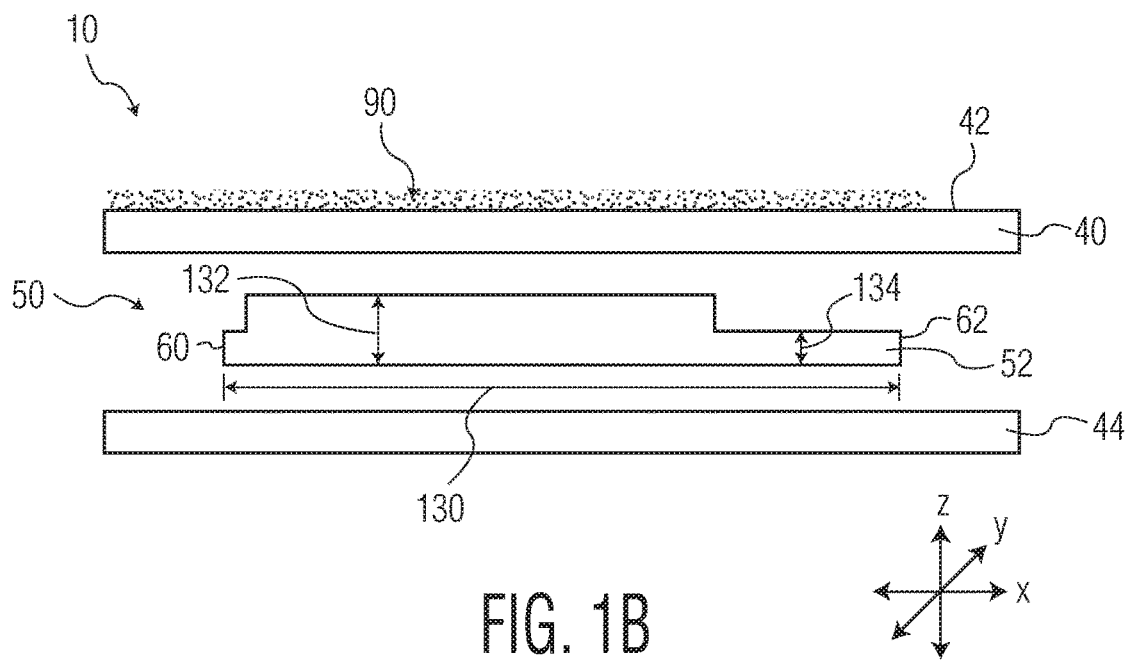
FIG. 1B is an exploded side view of the absorbent article of FIG. 1A.

Referring to FIGS. 1A and 1B, an absorbent article 10 of the present disclosure is exemplified in the form of a feminine hygiene product such as a menstrual pad or sanitary napkin. FIG. 1A provides a top down view of the exemplary embodiment of the absorbent article 10 and FIG. 1B provides an exploded side view of the absorbent article 10 of FIG. 1A. The absorbent article 10 can have a longitudinal direction (X), a transverse direction (Y), and a depth direction (Z). The absorbent article 10 can have a longitudinal axis 12 and a transverse axis 14. The absorbent article 10 can have an anterior region 20, a posterior region 22, and a central region 24 positioned between the anterior region 20 and the posterior region 22. Each of the anterior region 20, the posterior region 22, and the central region 24 can have a length in the longitudinal direction (X) of one-third of the total length in the longitudinal direction (X) of the absorbent article 10. When the absorbent article 10 is in use, the anterior region 20 can generally be placed towards the anterior region of the vulva region of the wearer, the posterior region 22 can generally be placed towards the perineum of the wearer, and the central region 24 can be positioned at the primary location of exudate discharge from the wearer. In such a placement of the absorbent article 10 on the wearer, the absorbent article 10 can conform to the body of the wearer, can provide leakage protection to the wearer, and can form a barrier completely surrounding the labia majora of the wearer. As a result, exudate discharged from the wearer will be confined to the absorbent article 10.

The absorbent article 10 can have a first transverse direction end edge 30, a second transverse direction end edge 32 opposed to the first transverse direction end edge 30, and a pair of opposing longitudinal direction side edges 34 extending between and connecting the first and second transverse direction end edges, 30 and 32. The absorbent article 10 can have a wearer facing, liquid permeable topsheet layer 40 and a garment facing, liquid impermeable backsheet layer 44. An absorbent system 50 can be positioned between the topsheet layer 40 and the backsheet layer 44. The topsheet layer 40 and the backsheet layer 44 can both extend beyond the outermost perimeter edge 58 of the absorbent system 50 and can be peripherally bonded together using known bonding techniques to form a sealed peripheral region. For example, the topsheet layer 40 and the backsheet layer 44 can be bonded together by adhesive bonding, ultrasonic bonding, or any other suitable bonding technique known in the art. A body adhesive 90 can be positioned on the body facing surface of the topsheet layer 40 in order to adhere the absorbent article 10 to the body of the wearer during usage of the absorbent article 10.

Figure 6A:
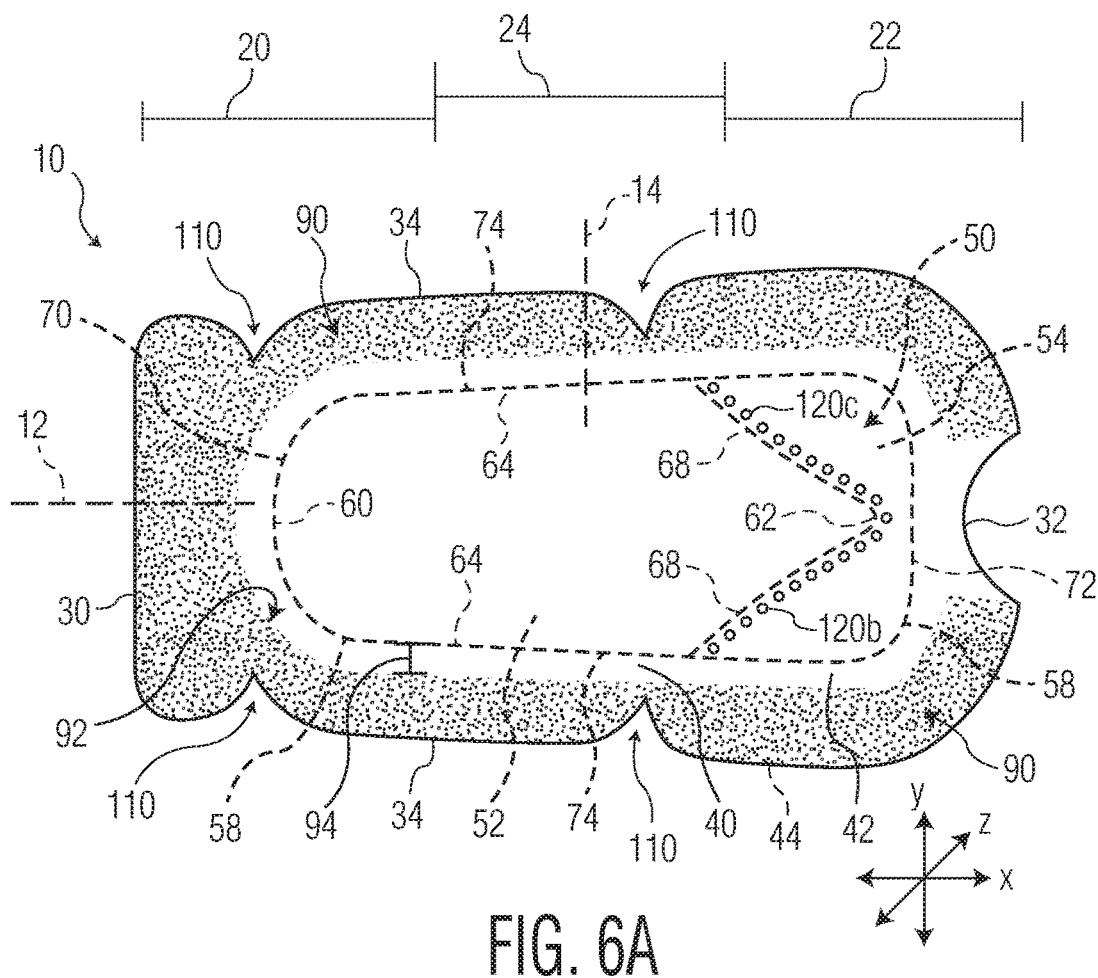
FIG. 6A is a top view of an exemplary embodiment of an absorbent article.
Figure 6B:
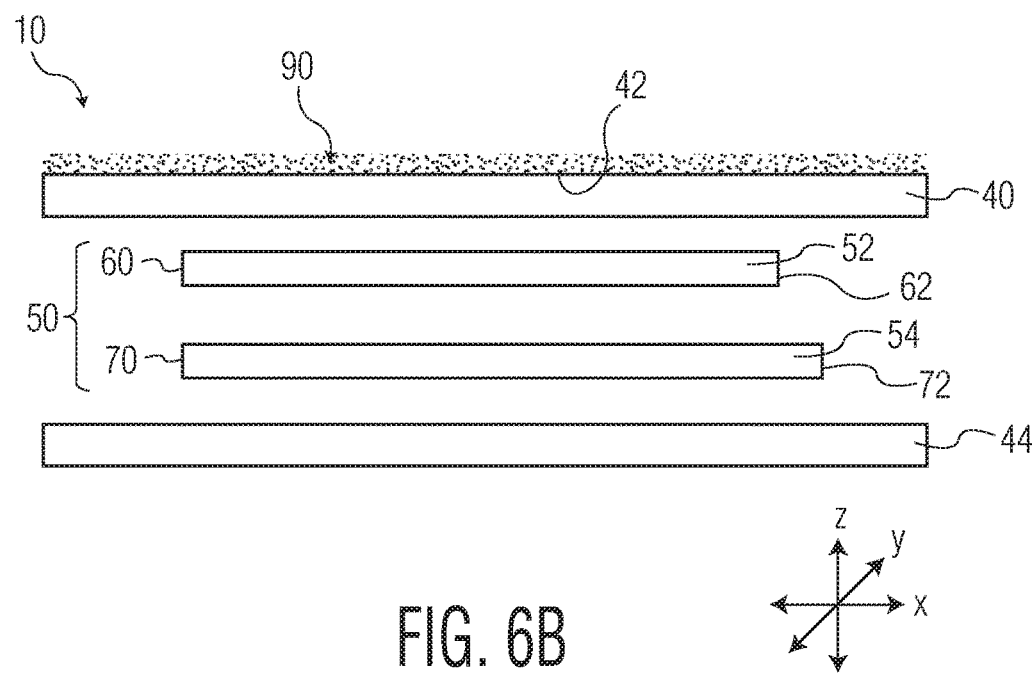
FIG. 6B is an exploded side view of the absorbent article of FIG. 6A.

The absorbent article 10 can have any shape as deemed suitable to provide a portion, the anterior region 20, which can be placed towards the anterior region of the vulva region of the wearer, a portion, the posterior region 22, which can be placed towards the perineum of the wearer, and another portion, the central region 24, which can be positioned at the primary location of exudate discharge from the wearer. In various embodiments, the shape of the absorbent article 10 can have a shape which provides symmetry about at least one axis, longitudinal 12 and/or transverse 14, of the absorbent article 10. In various embodiments, the shape of the absorbent article 10 can be one in which there is no symmetry of the absorbent article 10 about either of the axes, longitudinal 12 or transverse 14 of the absorbent article 10. In various embodiments, the absorbent article 10 can have a generally dog-bone shape, such as, for example, illustrated in FIG. 1A. By generally dog-bone shape it is meant a shape in which the longitudinal direction side edges 34 converge towards each other at a point in the longitudinal direction (X) of the absorbent article 10 to form a narrowest portion of the absorbent article 10. Generally, the dog-bone shape provides a cutout for the wearer's legs. By having an dog-bone shape the absorbent article 10 will not have to be attached to the legs of the wearer during usage of the absorbent article 10. An additional exemplary embodiment of a shape of an absorbent article 10 can be seen in the illustration of an absorbent article 10 of FIG. 6A. The absorbent article 10 illustrated in FIG. 6A provides for an absorbent article 10 in which the width in the transverse direction (Y) of the absorbent article 10 in the anterior region 20 is narrower than the width in the transverse direction (Y) of the absorbent article 10 in the posterior region 22 of the absorbent article 10. In various embodiments, a portion of the posterior region 22 of an absorbent article 10 can flex into the perineum of the wearer providing for a close to the body fit of the absorbent article 10. In various embodiments, the absorbent article 10 can have a width in the transverse direction (Y) that provides for a portion of the absorbent article 10 extending at least 10 mm beyond the labia majora of the wearer of the absorbent article 10. In various embodiments, the absorbent article 10 can have a width in the transverse direction (Y) from about 50 mm to about 150 mm. In various embodiments, the absorbent article 10 can have a width in the transverse direction (Y) which is uniform along the longitudinal axis 12 of the absorbent article 10. In various embodiments, the absorbent article 10 can have a width in the transverse direction (Y) which is variable along the longitudinal axis 12 of the absorbent article 10. In various embodiments, the absorbent article 10 can have a length in the longitudinal direction (X) from about 140 mm to about 200 mm. In various embodiments, the absorbent article 10 can have a length in the longitudinal direction (X) which is uniform along the transverse axis 14 of the absorbent article 10. In various embodiments, the absorbent article 10 can have a length in the longitudinal direction (X) which is variable along the transverse axis 14 of the absorbent article 10.

Each of these components of the absorbent article 10, as well as additional components, will be described in more detail herein.

Topsheet Layer:

The topsheet layer 40 defines a body facing surface 42 of the absorbent article 10 that may directly contact the body of the wearer and is liquid permeable to receive body exudates. The topsheet layer 40 is desirably provided for comfort and functions to direct body exudates away from the body of the wearer, through its own structure, and towards the absorbent system 50. The topsheet layer 40 desirably retains little to no liquid in its structure, so that it provides a relatively comfortable and non-irritating surface next to the skin of the wearer of the absorbent article 10.

The topsheet layer 40 can be a single layer of material, or alternatively, can be multiple layers that have been laminated together. The topsheet layer 40 can be constructed of any material such as one or more woven sheets, one or more fibrous nonwoven sheets, one or more film sheets, such as blown or extruded films, which may themselves be of single or multiple layers, one or more foam sheets, such as reticulated, open cell or closed cell foams, a coated nonwoven sheet, or a combination of any of these materials. Such combination can be adhesively, thermally, or ultrasonically laminated into a unified planar sheet structure to form a topsheet layer 40.

In various embodiments the topsheet layer 40 can be constructed from various nonwoven webs such as meltblown webs, spunbond webs, hydroentangled spunlace webs, or through air bonded carded webs. Examples of suitable topsheet layer 40 materials can include, but are not limited to, natural fiber webs (such as cotton), rayon, hydroentangled webs, bonded carded webs of polyester, polypropylene, polyethylene, nylon, or other heat-bondable fibers (such as bicomponent fibers), polyolefins, copolymers of polypropylene and polyethylene, linear low-density polyethylene, and aliphatic esters such as polylactic acid. Finely perforated films and net materials can also be used, as can laminates of/or combinations of these materials. An example of a suitable topsheet layer 40 can be a bonded carded web made of polypropylene and polyethylene such as that obtainable from Sandler Corp., Germany. U.S. Pat. No. 4,801,494 to Datta, et al., and U.S. Pat. No. 4,908,026 to Sukiennik, et al., and WO 2009/062998 to Texol teach various other topsheet materials that may be used as the topsheet layer 40, each of which is hereby incorporated by reference thereto in its entirety. Additional topsheet layer 40 materials can include, but are not limited to, those described in U.S. Pat. No. 4,397,644 to Matthews, et al., U.S. Pat. No. 4,629,643 to Curro, et al., U.S. Pat. No. 5,188,625 to Van Iten, et al., U.S. Pat. No. 5,382,400 to Pike, et al., U.S. Pat. No. 5,533,991 to Kirby, et al., U.S. Pat. No. 6,410,823 to Daley, et al., and U.S. Publication No. 2012/0289917 to Abuto, et al., each of which is hereby incorporated by reference thereto in its entirety.

The topsheet layer 40 should be selected such that the overall properties of the topsheet layer 40 allow the absorbent article 10 to move with the skin of the wearer during normal usage and normal movements by the wearer during use. By "normal movements by the wearer" it is meant any movement that normally occurs during usage of the absorbent article 10, including walking, running, sitting, standing, kneeling, riding a bicycle, exercising, playing sports, getting into and out of an automobile, and other similar movements, made by wearers when wearing an absorbent article. The topsheet layer 40 should not be too rigid, such that the absorbent article 10 detaches from the skin of the wearer during usage and should not be so flexible that the absorbent article would tend to bunch and twist during usage. The topsheet layer 40 should have sufficient flexibility to conform to the skin of the wearer. The absorbent article 10 should also have the ability to remain attached to the body of the wearer under moist or wet conditions. In various embodiments, the material forming the topsheet layer 40 can be stretchable and/or elastic.

In various embodiments, the topsheet layer 40 may contain a plurality of apertures formed therethrough to permit body exudates to pass more readily into the absorbent system 50. The apertures may be randomly or uniformly arranged throughout the topsheet layer 40. The size, shape, diameter, and number of apertures may be varied to suit an absorbent article's 10 particular needs.

In various embodiments, the tosphheet layer 40 can have a basis weight ranging from about 5, 10, 15, 20, or 25 gsm to about 50, 100, 120, 125, or 150 gsm. For example, in an embodiment, a topsheet layer 40 can be constructed from a through air bonded carded web having a basis weight ranging from about 15 gsm to about 100 gsm. In another example, a topsheet layer 40 can be constructed from a through air bonded carded web having a basis weight from about 20 gsm to about 50 gsm, such as a through air bonded carded web that is readily available from nonwoven material manufacturers, such as Xiamen Yanjan Industry, Beijing, DaYuan Nonwoven Fabrics, and others.

In various embodiments, the topsheet layer 40 can be at least partially hydrophilic. In various embodiments, a portion of the topsheet layer 40 can be hydrophilic and a portion of the topsheet layer 40 can be hydrophobic. In various embodiments, the portions of the topsheet layer 40 which can be hydrophobic can be either an inherently hydrophobic material or can be a material treated with a hydrophobic coating.

In various embodiments, the topsheet layer 40 can be a multicomponent topsheet layer 40 such as by having two or more different nonwoven or film materials, with the different materials placed in separate locations in the transverse direction (Y) of the absorbent article 10. For example, the topsheet layer 40 can be a two layer or multicomponent material having a central portion positioned along and straddling a longitudinal axis 12 of an absorbent article 10, with lateral side portions flanking and bonded to each side edge of the central portion. The central portion can be constructed from a first material and the side portions can be constructed from a material which can be the same as or different from the material of the central portion. In such embodiments, the central portion may be at least partially hydrophilic and the side portions may be inherently hydrophobic or may be treated with a hydrophobic coating. Examples of constructions of multi-component topsheet layers 40 are generally described in U.S. Pat. No. 5,961,505 to Coe, U.S. Pat. No. 5,415,640 to Kirby, and U.S. Pat. No. 6,117,523 to Sugahara, each of which is incorporated herein by reference thereto in its entirety.

In various embodiments, a central portion of a topsheet layer 40 can be positioned symmetrically about the absorbent article 10 longitudinal axis 12. Such central longitudinally directed central portion can be a through air bonded carded web ("TABCW") having a basis weight between about 15 and about 100 gsm. Previously described nonwoven, woven, and aperture film topsheet layer materials may also be used as the central portion of a topsheet layer 40. In various embodiments, the central portion can be constructed from a TABCW material having a basis weight from about 20 gsm to about 50 gsm such as is available from Xiamen Yanjan Industry, Beijing, DaYuan Nonwoven Fabrics, and others. Alternatively, aperture films, such as those available from such film suppliers as Texol, Italy and Tredegar, U.S.A. may be utilized. Different nonwoven, woven, or film sheet materials may be utilized as the side portions of the topsheet layer 40. The selection of such topsheet layer 40 materials can vary based upon the overall desired attributes of the topsheet layer 40. For example, it may be desired to have a hydrophilic material in the central portion and hydrophobic-barrier type materials in the side portions to prevent leakage and increase a sense of dryness in the area of the side portions. Such side portions can be adhesively, thermally, ultrasonically, or otherwise bonded to the central portion along or adjacent the longitudinally directed side edges of the central portion. Traditional absorbent article construction adhesive may be used to bond the side portions to the central portion. Either of the central portion and/or the side portions may be treated with surfactants and/or skin-health benefit agents, as are well known in the art.

Such longitudinally directed side portions can be of a single or multi-layered construction. In various embodiments, the side portions can be adhesively or otherwise bonded laminates. In various embodiments, the side portions can be constructed of an upper fibrous nonwoven layer, such as a spunbond material, laminated to a bottom layer of a hydrophobic barrier film material. Such a spunbond layer may be formed from a polyolefin, such as a polypropylene and can include a wetting agent if desired. In various embodiments, a spunbond layer can have a basis weight from about 10 or 12 gsm to about 30 or 70 gsm and can be treated with hydrophilic wetting agents. In various embodiments, a film layer may have apertures to allow fluid to permeate to lower layers, and may be either of a single layer or multi-layer construction. In various embodiments, such film can be a polyolefin, such as polyethylene having a basis weight from about 10 to about 40 gsm. Construction adhesive can be utilized to laminate the spunbond layer to the film layer at an add-on level of between about 0.1 gsm and 15 gsm. When a film barrier layer is used in the overall topsheet layer 40 design, it may include opacifying agents, such as film pigments, that can help the film in masking stains along the absorbent article 10 side edges, thereby serving as a masking element. In such a fashion, the film layer can serve to limit visualization of a fluid insult stain along the absorbent article 10 side edges when viewed from above the topsheet layer 40. The film layer may also serve as a barrier layer to prevent rewet of the topsheet layer 40 as well as to prevent the flow of fluid off the side edges of the absorbent article 10. In various embodiments, the side portions can be laminates such as a spunbond-meltblown-meltblown-spunbond layer ("SMMS") laminate, spunbond-film laminate, or alternatively, other nonwoven laminate combinations.

Absorbent System:

The absorbent system 50 is designed to absorb body exudates, including menstrual fluid, blood, urine, and other bodily fluids such as sweat and vaginal discharge. In various embodiments, the absorbent system 50 can include an absorbent core 52. In various embodiments, the absorbent system 50 can include an absorbent core 52 and a distribution layer 54. In various embodiments, the absorbent system 50 can include an absorbent core 52, a distribution layer 54, and a fluid intake layer 56.

Each layer of the absorbent system 50 can have any shape and configuration deemed suitable and can provide the absorbent system 50 with an overall shape and configuration. Such an overall shape and configuration of the absorbent system 50 can provide the absorbent system 50 with an overall perimeter edge 58. The perimeter edge 58 of the absorbent system 50 can be the perimeter edge of a layer (or a combination of portions of perimeter edges of different layers) of the absorbent system 50 that is the furthest from the intersection of the longitudinal axis 12 and the transverse axis 14. In various embodiments, the perimeter edge 58 of the absorbent system 50 can be contiguous with a perimeter edge of a single layer of the absorbent system 50. For example, in various embodiments, the absorbent system 50 may include an absorbent core 52 and the perimeter edge 58 of the absorbent system 50 can be contiguous with the perimeter edge of the absorbent core 52, such as, for example, illustrated in FIG. 1A. In various embodiments, the absorbent system 50 can include an absorbent core 52 and a distribution layer 54. In various embodiments, the distribution layer 54 may be larger in the longitudinal direction (X) and the transverse direction (Y) than the absorbent core 52 and in such embodiments the perimeter edge of the distribution layer 54 may extend further from the intersection of the longitudinal axis 12 and transverse axis 14 than the perimeter edge of the absorbent core 52. In such embodiments, the perimeter edge 58 of the absorbent system 50 can be contiguous with the perimeter edge of the distribution layer 54. As an additional example, in various embodiments, a portion of the perimeter edge 58 of the absorbent core 52 may align with a portion of the perimeter edge of the distribution layer 54 and a portion of the distribution layer 54 may extend beyond a portion of the perimeter edge of the absorbent core 52, such as, for example, illustrated in FIG. 2A. In such embodiments, the perimeter edge 58 of the absorbent system 50 may be defined by a combination of the portion of the perimeter edge of the distribution layer 54 extending beyond the absorbent core 52 and the combination of the aligned portions of perimeter edges of the absorbent core 52 and distribution layer 54. In various embodiments, the absorbent system 50 may be designed to have a distribution layer 54 and an absorbent core 52 wherein a portion of the absorbent core 52 can extend beyond a portion of a perimeter edge of the distribution layer 54, a portion of the distribution layer 54 can extend beyond a portion of a perimeter edge of the absorbent core 52, and a portion of each of the perimeter edges of the absorbent core 52 and distribution layer 54 may align with each other. In such embodiments, the perimeter edge 58 of the absorbent system 50 may formed from a combination of portions of the perimeter edges of each of the absorbent core 52 and distribution layer 54 as well as portions where the perimeter edges of each of the absorbent core 52 and distribution layer 54 can be aligned with each other.

The shape of the absorbent system 50 defined by the perimeter edge 58 can vary as desired and can comprise any one of various shapes including, but not limited to, triangular, tear-drop, rectangular, dog-bone, oval, oblong, hourglass, racetrack, and elliptical shapes as well as any other geometric shape as deemed suitable for the absorbent article 10 absorbent system 50. In various embodiments, the shape of the absorbent system 50 can have a shape which provides symmetry about at least one axis, longitudinal 12 and/or transverse 14, of the absorbent article 10. In various embodiments, the shape of the absorbent system 50 can be one in which there is no symmetry of the absorbent system 50 about either of the axes, longitudinal 12 or transverse 14 of the absorbent article 10. In various embodiments, the absorbent system 50 can have a total area of less than about 60, 65, 70, 75, or 80 cm$^2$.

The absorbent system 50 can have a width in the transverse direction (Y) as well as a length in the longitudinal direction (X). The width in the transverse direction (Y) and the length in the longitudinal direction (X) of the absorbent system 50 should be at least as wide and as long as the labia majora of the wearer of the absorbent article 10. In order to fit the majority of women, the length in the longitudinal direction (X) of the absorbent system 50 is greater than the width in the transverse direction (Y) of the absorbent system 50. Generally, for most women, the labia majora are generally between about 45 mm and about 90 mm in width and between about 50 mm and about 150 mm in length. Ideally, the absorbent system 50 is wider than the labia majora and slightly longer than the labia minora and slightly longer than or equal to the labia majora.

The width in the transverse direction (Y) of at least a portion of the absorbent system 50 can be from about 30, 40, or 50 mm to about 60, 70, 80, 90, or 100 mm. In various embodiments, the width in the transverse direction (Y) of the absorbent system 50 can be uniform along the longitudinal axis 12 of the absorbent system 50. In various embodiments, the width in the transverse direction (Y) of the absorbent system 50 can be variable along the longitudinal axis 12 of the absorbent system 50. In various embodiments, the width in the transverse direction (Y) of the absorbent system 50 in the posterior region 22 of the absorbent article 10 can be the same as the width in the transverse direction (Y) of the absorbent system 50 in the anterior region 20 of the absorbent article 10. In various embodiments, the width in the transverse direction (Y) of the absorbent system 50 in the posterior region 22 of the absorbent article 10 can be greater than the width in the transverse direction (Y) of the absorbent system 50 in the anterior region 20 of the absorbent article 10. In various embodiments, the width in the transverse direction (Y) of the absorbent system 50 in the posterior region 22 of the absorbent article 10 can be greater than the width in the transverse direction (Y) of the absorbent system 50 in the central region 24 of the absorbent article 10.

The length in the longitudinal direction (X) of at least a portion of the absorbent system 50 can be from about 90, 100, 110, or 120 mm to about 130, 140, 150, or 160 mm. In various embodiments, the length in the longitudinal direction (X) of the absorbent system 50 can be uniform along the transverse axis 14 of the absorbent system 50. In various embodiments, the length in the longitudinal direction (X) of the absorbent system 50 can be variable along the transverse axis 14 of the absorbent system 50.

The absorbent system 50 can have a height in the depth direction (Z) of the absorbent article 10. In various embodiments, the height of at least a portion of the absorbent system 50 can be from about 2, 3, 4, or 5 mm to about 6, 7, 8, 9, or 10 mm. In various embodiments, the height of the absorbent system 50 in the depth direction (Z) of the absorbent article 10 is variable. In various embodiments, the variability of height in the depth direction (Z) can be a gradual change in height from one portion of the absorbent system 50 to another portion of the absorbent system 50. In various embodiments, the variability of height in the depth direction (Z) can be an abrupt change in height from one portion of the absorbent system 50 to another portion of the absorbent system 50. In various embodiments, the height of the absorbent system 50 can vary in the longitudinal direction (X). In various embodiments, the height of the absorbent system 50 can vary in the transverse direction (Y). In various embodiments, the height of the absorbent system 50 can vary in the longitudinal direction (X) and in the transverse direction (Y). In various embodiments in which the absorbent system 50 can be designed with an absorbent core 52, the height of the absorbent core 52 can vary to provide an absorbent system 50 with variable height. For example, as illustrated in FIG. 1B, the absorbent system 50 has an absorbent core 52 wherein a first portion of the absorbent core 52 has a first height 132 and a second portion of the absorbent core 52 has a second height 134 wherein the first height 132 and the second height 134 are not the same. The heights, 132 and 134, of the two respective portions of the absorbent core 52 are measured as the distance from the body facing surface of the absorbent core 52 to the garment facing surface of the absorbent core 52 in each of the respective portions of the absorbent core 52. In various embodiments, such as, for example, illustrated in FIG. 2B, an absorbent system 50 can have an absorbent core 52 and a distribution layer 54. In various embodiments, the height of the absorbent core 52 in the depth direction (Z) can be the same as the height of the distribution layer 54 in the depth direction (Z). In various embodiments, the height of the absorbent core 52 in the depth direction (Z) can be greater than the height of the distribution layer 54 in the depth direction (Z). In various embodiments, the combined height of the absorbent core 52 and the distribution layer 54 in the depth direction (Z) can be greater than the height of the distribution layer 54 only in the depth direction (Z). In embodiments in which an absorbent system 50 has an absorbent core 52 and a distribution layer 54, at least a portion of the distribution layer 54 can extend beyond the perimeter edge of the absorbent core 52 and the combined height of the overlapping absorbent core 52 and distribution layer 54 can be greater than the height of the portion of the distribution layer 54 extending beyond the perimeter edge of the absorbent core 52. In various embodiments, the height of a portion of the absorbent system 50 in the anterior region 20 of the absorbent article 10 can be greater than the height of a portion of the absorbent system 50 in the posterior region 22 of the absorbent article 10.

Absorbent Core:

An absorbent system 50 having an absorbent core 52 can be positioned between the topsheet layer 40 and the backsheet layer 44. The absorbent core 52 can generally be any single layer structure or combination of layer components, which can demonstrate some level of compressibility, conformability, be non-irritating to a wearer's skin, and capable of absorbing and retaining liquids and other body exudates. In various embodiments, the absorbent core 52 can be formed from a variety of different materials and can contain any number of desired layers. In various embodiments in which the absorbent core 52 is a multi-layered structure, each of the layers can contain similar materials or different materials. For example, the absorbent core 52 can include one or more layers (e.g., two layers) of absorbent web material of cellulosic fibers (e.g., wood pulp fibers), other natural fibers, synthetic fibers, woven or nonwoven sheets, scrim netting, or other stabilizing structures, superabsorbent material, binder materials, surfactants, selected hydrophobic and hydrophilic materials, pigments, lotions, odor control agents or the like, as well as combinations thereof. In an embodiment, the absorbent web material can include a matrix of cellulosic fluff and can also include superabsorbent material. The cellulosic fluff can comprise a blend of wood pulp fluff. An example of a wood pulp fluff can be identified with the trade designation NB 416, available from Weyerhaeuser Corp., and is a bleached, highly absorbent wood pulp containing primarily soft wood fibers. By way of example, suitable materials and/or structures for the absorbent core 52 can include, but are not limited to, those described in U.S. Pat. No. 4,610,678 to Weisman, et al., U.S. Pat. No. 6,060,636 to Yahiaoui, et al., U.S. Pat. No. 6,610,903 to Latimer, et al., U.S. Pat. No. 7,358,282 to Krueger, et al., and U.S. Publication No. 2010/0174260 to Di Luccio, et al., each of which is hereby incorporated by reference thereto in its entirety.

In various embodiments, if desired, the absorbent core 52 can include an optional amount of superabsorbent material. Examples of suitable superabsorbent material can include poly(acrylic acid), poly(methacrylic acid), poly(acrylamide), poly(vinyl ether), maleic anhydride copolymers with vinyl ethers and α-olefins, poly(vinyl pyrrolidone), poly (vinylmorpholinone), poly(vinyl alcohol), and salts and copolymers thereof. Other superabsorbent materials can include unmodified natural polymers and modified natural polymers, such as hydrolyzed acrylonitrile-grafted starch, acrylic acid grafted starch, methyl cellulose, chitosan, carboxymethyl cellulose, hydroxypropyl cellulose, and natural gums, such as alginates, xanthan gum, locust bean gum, and so forth. Mixtures of natural and wholly or partially synthetic superabsorbent polymers can also be useful. The superabsorbent material can be present in the absorbent core 52 in any amount as desired.

Regardless of the combination of absorbent materials used in the absorbent core 52, the absorbent materials can be formed into a web structure by employing various conventional methods and techniques. For example, the absorbent web can be formed by techniques such as, but not limited to, a dry-forming technique, an air forming technique, a wet forming technique, a foam forming technique, or the like, as well as combinations thereof. A coform nonwoven material can also be employed. Methods and apparatus for carrying out such techniques are well known in the art.

Figure 2A:
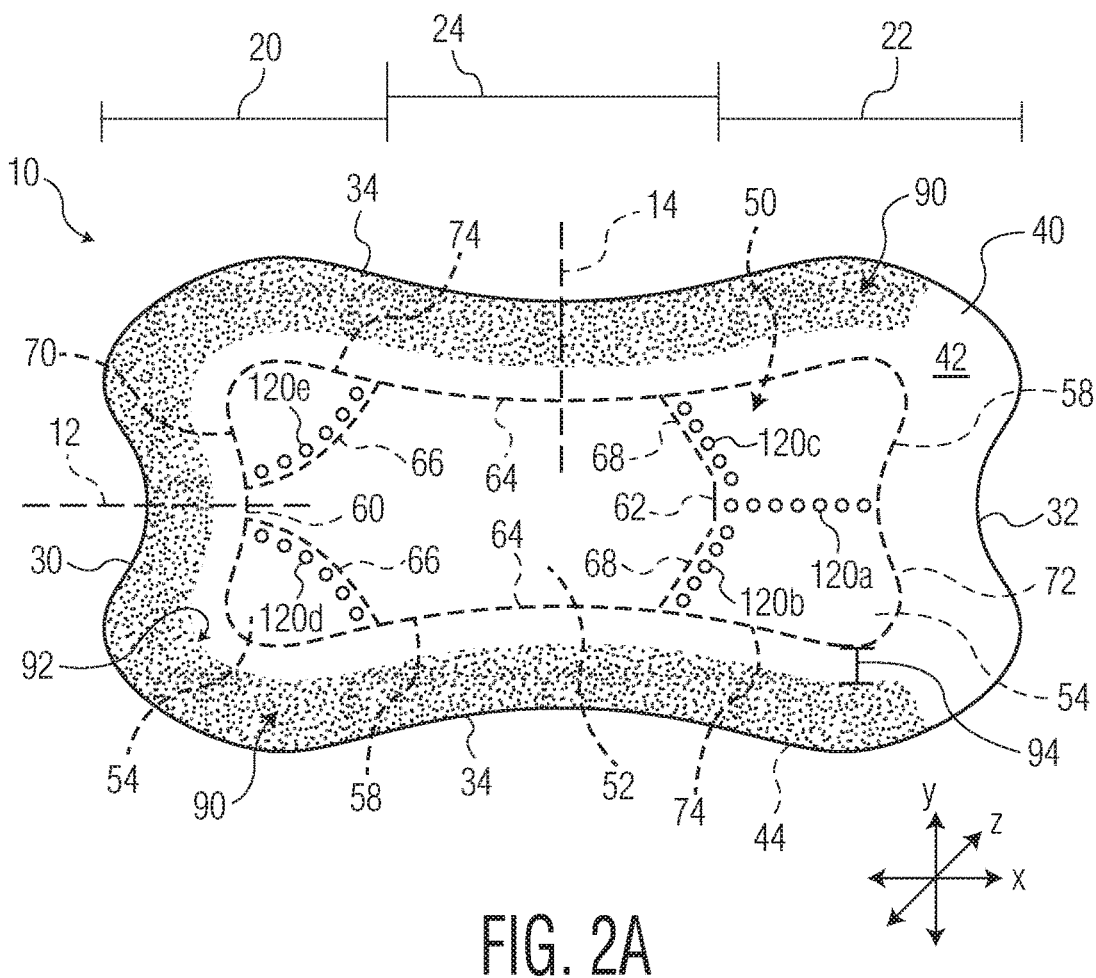
FIG. 2A is a top view of an exemplary embodiment of an absorbent article.
Figure 2B:
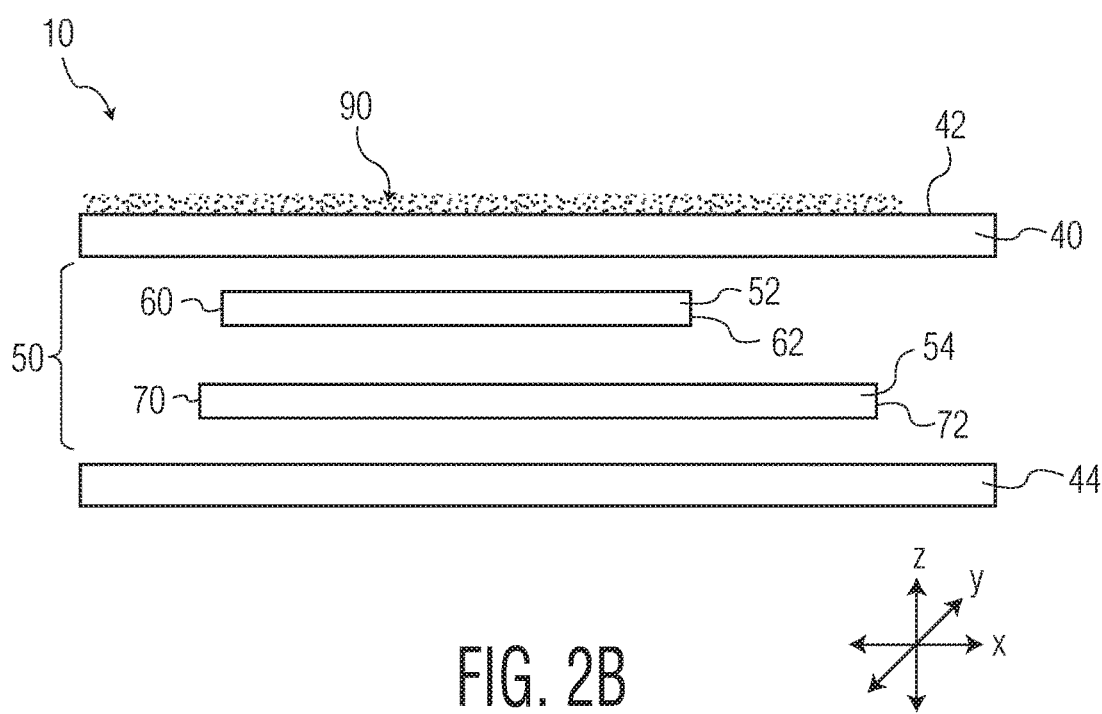
FIG. 2B is an exploded side view of the absorbent article of FIG. 2A.

The absorbent core 52 can have a first transverse direction core end edge 60 positioned between the transverse axis 14 and the first transverse direction end edge 30 of the absorbent article 10 as well as a second transverse direction core end edge 62 positioned between the transverse axis 14 and the second transverse direction end edge 32 of the absorbent article 10. The absorbent core 52 can also have a pair of opposing longitudinal direction core side edges 64. The absorbent core 52 can be provided in any shape as deemed suitable for the absorbent article 10 such as, but not limited to, oblong, oval, rectangular, tear-dropped, hourglass, and racetrack. In various embodiments, the shape of the absorbent core 52 can have a shape which provides symmetry about at least one axis, longitudinal 12 and/or transverse 14, of the absorbent article 10. In various embodiments, the shape of the absorbent core 52 can be one in which there is no symmetry of the absorbent core 52 about either of the axes, longitudinal 12 or transverse 14 of the absorbent article 10. Referring to FIG. 1A, the absorbent core 52 is provided as a generally hourglass shape. In various embodiments, the absorbent core 52 may have any polygonal shape as desired such as, for example, the absorbent core 52 can have a generally hexagonal or a generally octagonal shape. The absorbent core 52 can have any polygonal shape as deemed suitable and such shapes may define an absorbent core 52 having additional sidewalls. For example, as illustrated in FIG. 2A, an absorbent system 50 has an absorbent core 52 and a distribution layer 54. The absorbent core 52 as illustrated in FIG. 2A has a pair of transverse direction core end edges, 62 and 64, and a pair of longitudinal direction core side edges 64 as well as a pair of angled sidewalls 66 which can define the shape of the core 52 between the first transverse direction core end edge 60 and the longitudinal direction core side edges 64 and a pair of angled sidewalls 68 which can define the shape of the core 52 between the second transverse direction core end edge 62 and the longitudinal direction core side edges 64.

In various embodiments, at least a portion of the absorbent core 52 can have a length in the longitudinal direction (X) from about 65, 70, 75 or 80 mm to about 90, 100, 110, 115, 120, 130, 140, 150, or 160 mm. In various embodiments, the length in the longitudinal direction (X) of the absorbent core 52 can be uniform along the transverse axis 14 of the absorbent article 10. In various embodiments, the length in the longitudinal direction (X) of the absorbent core 52 can be variable along the transverse axis 14 of the absorbent article 10. In various embodiments, at least a portion of the absorbent core 52 can have a width in the transverse direction (Y) of from about 1, 2, 3, 4, 5, 6, 7, 8, 9, 10, 20, or 30, to about 35, 40, 50, 60, 70, 80, 90, or 100 mm. In various embodiments, the width in the transverse direction (Y) of the absorbent core 52 can be uniform along the longitudinal axis 12 of the absorbent core 52. In various embodiments, the width in the transverse direction (Y) of the absorbent core 52 can be variable along the longitudinal axis 12 of the absorbent core 52. In various embodiments, the second transverse direction core end edge 62 of the absorbent core 52 can have a width in the transverse direction (Y) from about 1, 2, 3, or 4 mm to about 5, 6, 7, 8, 9, or 10 mm. In various embodiments, therefore, the absorbent core 52 of the absorbent system 50 can have a width in the transverse direction (Y) at the second transverse direction core end edge 62 which is smaller than a width in the transverse direction (Y) of the absorbent core 52 at the transverse axis 14 of the absorbent article 10. Referring to FIG. 1B, in various embodiments, the absorbent core 52 can have a variable height in the depth direction (Z) of the absorbent article 10. In various embodiments, the variability in height in the depth direction (Z) of the absorbent core 52 can be an abrupt transition from one portion of the absorbent core 52 to another portion of the absorbent core 52. In various embodiments, the variability in height in the depth direction (Z) of the absorbent core 52 can be a gradual transition from one portion of the absorbent core 52 to another portion of the absorbent core 52. Referring to FIGS. 2B, 3B, 4B, 5B, and 6B, in various embodiments, the absorbent core 52 can have a uniform height in the depth direction (Z) of the absorbent article 10.

Distribution Layer:

In various embodiments, the absorbent system 50 can have a distribution layer 54 positioned below the absorbent core 52 in the depth direction (Z) of the absorbent article 10 such that the distribution layer 54 is between the absorbent core 52 and the backsheet layer 44 such as, for examples, illustrated in FIGS. 2A, 2B, 3A, 3B, 4A, 4B, 5A, 5B, 6A, and 6B. The distribution layer 54 can increase absorbency of the absorbent article 10. The distribution layer 54 can be constructed of various materials such as, but not limited to, hydroentangled webs, through air bonded carded webs, cellulosic fluff based materials, meltblown webs, and meltblown microfiber webs. The distribution layer 54 can include a hydrophilic material. In various embodiments, the distribution layer 54 can have a topographical texture such as, for example, a corrugation pattern.

In various embodiments, the distribution layer 54 can have a density of greater than about 0.1 grams per cubic centimeter. The density can be calculated utilizing the formula: density=basis weight (gsm)/thickness (mm)/1000. In various embodiments, the distribution layer 54 can have a basis weight from about 10, 20, 25, 30 or 50 gsm to about 60, 70, 80, 90, 100, 120, 140, 150, 160, 180 or 200 gsm.

In various embodiments, the distribution layer 54 can be a hydroentangled web. The hydroentangled web can include a hydroentangled spunbond material and a pulp material. The hydroentangled spunbond material can include a polypropylene material. The spunbond material can be present in an amount from about 10% or 15% to about 20% or 25% of the hydroentangled web. The pulp material can be present in an amount from about 75% or 80% to about 85%, 90% or 100% of the hydroentangled web. The hydroentangled web can have a basis weight from about 30 or 60 gsm to about 90, 200, or 300 gsm. Without being bound by theory, it is believed that a higher basis weight hydroentangled web can improve the absorbency of the distribution layer 54. It is further believed that an improved absorbency of the distribution layer 54 can further result in an improved fluid retention capacity of the absorbent article 10. The basis weight of the hydroentangled web can be balanced with the desired flexibility of the absorbent article 10. In various embodiments, the distribution layer 54 can be a pulp sheet material. In such embodiments, the distribution layer 54 can contain 100% pulp material. In such embodiments, the distribution layer 54 can have a basis weight from about 30 or 60 gsm to about 90, 200 or 300 gsm. In various embodiments, the distribution layer 54 can include a bicomponent fluid distribution layer, which can increase absorbency by providing a high void space and may be made of a through air bonded carded web, having a basis weight, in an embodiment, of between about 25 gsm and 100 gsm. In various embodiments, the distribution layer 54 can be constructed of a superabsorbent polymer-containing compressed sheet. In such embodiments, the superabsorbent polymer-containing compressed sheet can be a cellulosic fluff based material that can be a combination of cellulosic pulp and SAP enclosed with a tissue carrier and having a basis weight from about 40 to about 400 gsm. In various embodiments, the distribution layer 54 can be a meltblown microfiber web of polypropylene material and can have a basis weight from about 10 or 20 gsm to about 30, 50 or 100 gsm. In various embodiments, the meltblown microfiber web can be treated with wetting agents for adequate handling of body exudates. Examples of wetting agents can include, but are not limited to, surface active agents (or surfactants) having a hydrophilic lipophilic balance (HLB) of at least 6, 7 or 18. A variety of surfactants can be used and can include, but are not limited to, anionic, cationic, or neutral from a charge standpoint. Mixtures of surfactants and other wetting agents can also be used. A wetting agent add-on can range from about 0.1 or 0.2% to about 5 or 10%. In various embodiments, an add-on amount can be higher than 10%. For example, the meltblown microfiber web can be treated to impart hydrophlicity by either Aerosol GPG of Cytec or Ahcovel Base N-62 for example. Such material is available from Yuhan-Kimberly Ltd., Seoul, Korea and FIberTex, Malaysia.

The distribution layer 54 can have a first transverse direction distribution layer end edge 70 and a second transverse direction distribution layer end edge 72 as well as a pair of opposing longitudinal direction distribution layer side edges 74. The first transverse direction distribution layer end edge 70 can be positioned between the transverse axis 14 and the first transverse direction end edge 30 of the absorbent article 10. The second transverse direction distribution layer end edge 72 can be positioned between the transverse axis and the second transverse direction end edge 32 of the absorbent article 10. In various embodiments, the distribution layer 54 can have a size dimension at least a portion of which can be larger than a size dimension of the absorbent core 52. In various embodiments, at least a portion of the distribution layer 54 can have a length in the longitudinal direction (X) which can be longer than the length in the longitudinal direction (X) of the absorbent core 52. In various embodiments, at least a portion of the distribution layer 54 can have a width dimension in the transverse direction (Y) in which at least a portion of the distribution layer 54 can be wider than a portion of the absorbent core 52 in the same plane along the longitudinal axis 12 of the absorbent article 10.

The distribution layer 54 can be provided in any shape as deemed suitable for the absorbent article 10 such as, but not limited to, oblong, oval, rectangular, tear-dropped, hourglass, and racetrack. In various embodiments, the shape of the distribution layer 54 can have a shape which provides symmetry about at least one axis, longitudinal 12 and/or transverse 14, of the absorbent article 10. In various embodiments, the shape of the distribution layer 54 can be one in which there is no symmetry of the distribution layer 54 about either of the axes, longitudinal 12 or transverse 14 of the absorbent article 10. Referring to FIG. 2A, the distribution layer 54 is provided as a generally hourglass shape. In various embodiments, the distribution layer 54 may have any polygonal shape as desired.

In various embodiments, at least a portion of the distribution layer 54 can have a length in the longitudinal direction (X) from about 65, 70, 75 or 80 mm to about 90, 100, 110, 115, 120, 130, 140, 150, or 160 mm. In various embodiments, the length in the longitudinal direction (X) of the distribution layer 54 can be uniform along the transverse axis 14 of the absorbent article 10. In various embodiments, the length in the longitudinal direction (X) of the distribution layer 54 can be variable along the transverse axis 14 of the absorbent article 10. In various embodiments, at least a portion of the distribution layer 54 can have a width in the transverse direction (Y) of from about 1, 2, 3, 4, 5, 6, 7, 8, 9, 10, 20, or 30, to about 35, 40, 50, 60, 70, 80, 90, or 100 mm. In various embodiments, the width in the transverse direction (Y) of the distribution layer 54 can be uniform along the longitudinal axis 12 of the distribution layer 54. In various embodiments, the width in the transverse direction (Y) of the distribution layer 54 can be variable along the longitudinal axis 12 of the distribution layer 54. In various embodiments, the distribution layer 54 can have a uniform height in the depth direction (Z) of the absorbent article 10. In various embodiments, the distribution layer 54 can have a variable height in the depth direction (Z) of the absorbent article 10. In various embodiments, the variability in height in the depth direction (Z) can be either a gradual transition or an abrupt transition from one portion of the distribution layer 54 to another portion of the distribution layer 54.

Figure 4A:
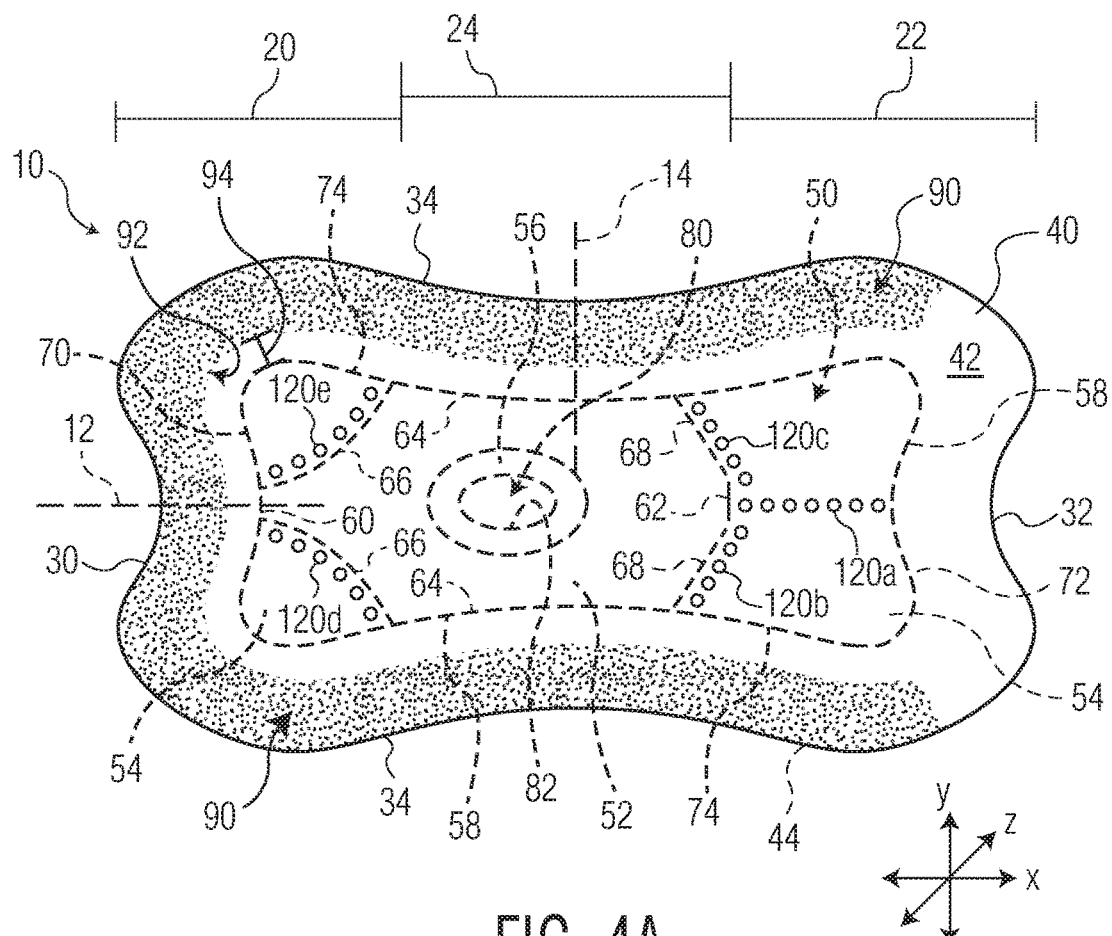
FIG. 4A is a top view of an exemplary embodiment of an absorbent article.
Figure 4B:
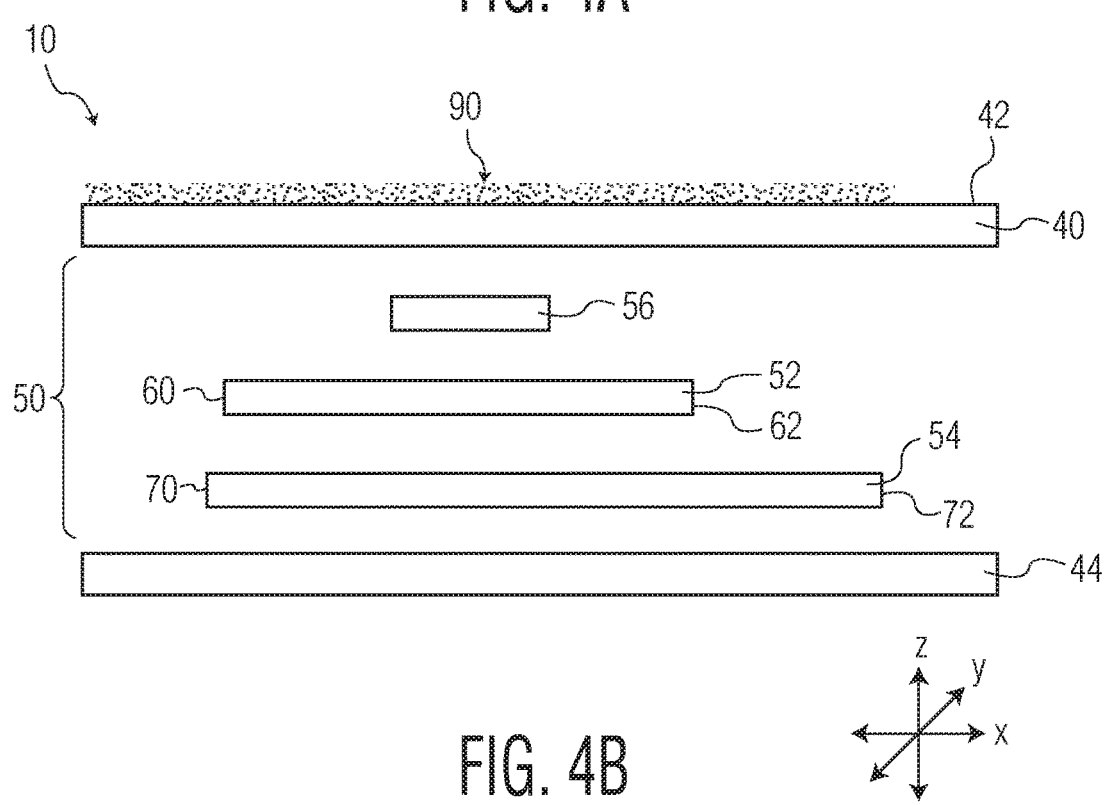
FIG. 4B is an exploded side view of the absorbent article of FIG. 4A.

Fluid Intake Layer:

In various embodiments, the absorbent system 50 can include a fluid intake layer 56 such as, for example, illustrated in FIGS. 4A and 4B. The fluid intake layer 56 can provide the absorbent article 10 with a raised portion which can improve the vertical absorption capability in the depth direction (Z) of the absorbent article. The raised portion can allow body exudates to pass through the topsheet layer 20 and directly to the absorbent core 52 where the body exudates can be quickly absorbed by the absorbent core 52. Thus, it can be possible to minimize or prevent body exudates from leaking or oozing outwardly from the absorbent article 10 prior to the body exudates being ultimately absorbed into the absorbent system 50.

The fluid intake layer 56 can generally have any shape and/or size desired. In various embodiments, the fluid intake layer 56 can have a curved rectangular, oval, circular, or oblong shape. In various embodiments, the shape of the fluid intake layer 56 can have a shape which provides symmetry about at least one axis, longitudinal 12 and/or transverse 14, of the absorbent article 10. In various embodiments, the shape of the fluid intake layer 56 can be one in which there is no symmetry of the fluid intake layer 56 about either of the axes, longitudinal 12 or transverse 14. In various embodiments, the fluid intake layer 56 can have a longitudinal length from about 10, 20, or 30 mm to about 40, 50, 60 or 70 mm and a transverse width from about 10, 15 or 20 mm to about 25, 30, or 35 mm. The fluid intake layer 56 can have a basis weight from about 10, 25, or 100 gsm to about 150, 200, 250, or 300 gsm. The body facing surface of the absorbent article 10 can have a total surface area. The body facing surface of the fluid intake layer 56 can have a surface area which is smaller than the total surface area of the absorbent article 10. In comparison to the total surface area of the absorbent article 10, the body facing surface of the fluid intake layer 56 can have a surface area from about 5 or 10% to about 15 or 20%.

Any of a variety of nonwoven materials can be capable of being used for the fluid intake layer 56. The nonwoven materials may be synthetic, cellulosic, or a combination of synthetic and cellulosic materials. For example, the fluid intake layer 56 can be constructed utilizing an airlaid, spunbond, tissue, meltblown, spunbond-meltblown-spunbond, foam or TABCW material. In various embodiments, the fluid intake layer 56 can be at least partially hydrophilic. In various embodiments, the hydrophilicity of the fluid intake layer 56 can be increased or created via treatment of the fluid intake layer 56 with surfactants.

The fluid intake layer 56 can be located at various positions along the longitudinal (X) and transverse (Y) directions of the absorbent article 10 depending upon the primary location of body exudate intake or the purpose for which the absorbent article 10 is being used. For example, in various embodiments, the fluid intake layer 56 can be positioned so that it can be in substantial alignment with the longitudinal axis 12 and the transverse axis 14 of the absorbent article 10. This allows the fluid intake layer 56 to be centrally disposed so that it can be positioned below the main point of body exudate discharge and so that it can act as the primary body exudate receiving area for the absorbent article 10.

However, centralized positioning of the fluid intake layer 56 is not required, and in various embodiments, depending on the primary location where body exudate intake might occur, the fluid intake layer 56 may be substantially aligned with the longitudinal axis 12 only. Thus, in various embodiments, the fluid intake layer 40 may be shifted in the longitudinal direction (L) towards either transverse direction end edge, 30 or 32, of the absorbent article 10, so that the fluid intake layer 56 is not in substantial alignment with the transverse axis 14.

In various embodiments, to further enhance the ability of the absorbent article 10 to transfer body exudates in the depth (Z) direction from the topsheet layer 30 toward any lower layers in the absorbent article 10 as well as to enhance the ability of the fluid intake layer 56 to conform to the wearer's body based on its ability to bend, the fluid intake layer 56 can have an opening 80 in the fluid intake layer 56 which can be any suitable shape, such as ovular, circular, rectangular, square, triangular, etc. In various embodiments, the shape of the opening 80 can have a shape which provides symmetry about at least one axis, longitudinal 12 and/or transverse 14, of the absorbent article 10. In various embodiments, the shape of the opening 80 can be one in which there is no symmetry of the opening 80 about either of the axes, longitudinal 12 or transverse 14 of the absorbent article 10. In various embodiments, the opening 80 in the fluid intake layer 56 can be elongate and can be oriented in the longitudinal direction of the absorbent article 10. The opening 80 of the fluid intake layer 56 can be bounded by a perimeter 82 which can form an inner border or inner edge of the fluid intake layer 56. The opening 80 of the fluid intake layer 56 can leave a portion of the absorbent core 52 exposed and visible due to the lack of presence of the material, i.e., a void space, of the fluid intake layer 56 at the opening 80. In various embodiments, the perimeter 82 of the opening 80 of the fluid intake layer 56 can be bonded to another layer of the absorbent article 10 such as, for example, the absorbent core 52. Such bonding can occur via any method deemed suitable such as adhesive bonding, ultra-sonic bonding, thermal bonding, pressure bonding, etc.

The opening 80 can be located at various positions along the longitudinal and transverse directions of the fluid intake layer 56 depending upon the primary location of body exudate intake or the purpose for which the absorbent article 10 is being used. For example, in various embodiments, the fluid intake layer 56 and the opening 80 in the fluid intake layer 56 can be positioned so that it is in substantial alignment with the longitudinal axis 12 and the transverse axis 14 of the absorbent article 10. This allows the opening 80 to be centrally disposed so that it can be positioned below the main point of body exudate discharge and so that it can act as the primary body exudate receiving area for the absorbent article 10.

However, centralized positioning of the fluid intake layer 56 and the opening 80 of the fluid intake layer 56 is not required, and in various embodiments, depending on the primary location where body exudate intake might occur, the fluid intake layer 56 and the opening 80 of the fluid intake layer 56 may be substantially aligned with the longitudinal axis 12 only. Thus, in various embodiments, the fluid intake layer 56 and the opening 80 of the fluid intake layer 56 may be shifted in the longitudinal direction towards either transverse direction end edge, 30 or 32, of the absorbent article 10, so that the opening 80 of the fluid intake layer 56 is not in substantial alignment with the transverse axis 14.

The opening 80 in the fluid intake layer 56 can have a longitudinal length from about 5, 10, 15, 20, 25, or 30 mm to about 35, 40, 45, or 50 mm and can have a transverse width from about 5, 10 or 15 mm to about 20 or 25 mm. The opening 80 in the fluid intake layer 56 can have a length that is from about 15, 20 or 25% to about 70, 75, or 80% of the overall longitudinal length of the fluid intake layer 56 in the longitudinal direction (X). The opening 80 in the fluid intake layer 56 can have a width that can be from about 20, 25 or 30% to about 70, 75 or 80% of the overall width of the fluid intake layer 56 in the transverse direction (Y). The opening 80 in the fluid intake layer 56 can serve to funnel and direct body exudates from the topsheet layer 40 and towards lower layers of the absorbent article 10 in the depth (Z) direction. The opening 80 in the fluid intake layer 56 can also form a cup or well-like structure for holding body exudates and preventing its leakage away from a central region of the absorbent article 10 and towards the edges of the absorbent article 10.

Backsheet Layer:

The backsheet layer 44 is generally liquid impermeable and is the portion of the absorbent article 10 which faces the garments of the wearer. The backsheet layer 44 can permit the passage of air or vapor out of the absorbent article 10 while still blocking the passage of liquids. Any liquid impermeable material may generally be utilized to form the backsheet layer 44. The liquid impermable layer 44 can be composed of a single layer or multiple layers, and these one or more layers can themselves comprise similar or different materials. Suitable material that may be utilized can be a microporous polymeric film, such as a polyolefin film or polyethylene or polypropylene, nonwovens, and nonwoven laminates, and film/nonwoven laminates. The particular structure and composition of the backsheet layer 44 can be selected from various known films and/or fabrics with the particular material being selected as appropriate to provide the desired level of liquid barrier, strength, abrasion resistance, tactile properties, aesthetics, and so forth. In various embodiments, a polyethylene film can be utilized that can have a thickness in the range of from about 0.2 or 0.5 mils to about 3.0 or 5.0 mils. An example of a backsheet layer 44 can be a polyethylene film such as that obtainable from Pliant Corp., Schaumburg, IL, USA. Another example can include calcium carbonate-filled polypropylene film. In still another embodiment, the backsheet layer 44 can be a hydrophobic nonwoven material with water barrier properties such as a nonwoven laminate, an example of which can be a spunbond, meltblown, meltblown, spunbons, four-layered laminate.

In various embodiments, the backsheet layer 44 can be a two layer construction, including an outer layer material and an inner layer material which can be bonded together. The outer layer can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer can be a 20 gsm spunbond polypropylene non-woven web. The inner layer can be either vapor permeable (i.e., "breathable") or vapor impermeable. The inner layer may be manufactured from a thin plastic film, although other liquid impermeable materials may also be used. The inner layer can inhibit liquid body exudates from leaking out of the absorbent article 10 and wetting articles, such as bed sheets and clothing, as well as the wearer and caregiver. An example of a material for an inner layer can be a printed 19 gsm Berry Plastics XP-8695H film or equivalent commercially available from Berry Plastics Corporation, Evansville, IN, U.S.A.

The backsheet layer 44 can, therefore, be of a single or multiple layer construction, such as of multiple film layers or laminates of film and nonwoven fibrous layers. Suitable backsheet layers 44 can be constructed from materials such as those described in U.S. Pat. No. 4,578,069 to Whitehead, et al., U.S. Pat. No. 4,376,799 to Tusim, et al., U.S. Pat. No. 5,695,849 to Shawver, et al., U.S. Pat. No. 6,075,179 to McCormack, et al., and U.S. Pat. No. 6,376,095 to Cheung, et al., each of which are hereby incorporated by reference thereto in its entirety.

The backsheet layer 44 should be selected such that the overall properties of the backsheet layer 44 allow the absorbent article 10 to move with the skin of the wearer during normal usage and normal movements by the wearer during use. The backsheet layer 44 should not be too rigid, such that the absorbent article 10 detaches from the skin of the wearer during usage and should not be so flexible that the absorbent article would tend to bunch and twist during usage. The backsheet layer 44 should have sufficient flexibility to conform to the skin of the wearer. The absorbent article 10 should also have the ability to remain attached to the body of the wearer under moist or wet conditions.

The backsheet layer 44 may form a portion of the garment-facing side of the absorbent article 10 when worn by a wearer. The backsheet layer 44 should be selected such that the garment facing surface of the backsheet layer 44 will freely move against the undergarment or clothing of the wearer. One way to achieve this result is to select a backsheet layer 44 material which will have a low coefficient of friction on the garment facing surface of the backsheet layer 44. This will allow the garment facing surface of the backsheet layer 44 to freely move against the undergarment or other clothing of the wearer. If the garment facing surface of the backsheet layer 44 does not freely move against the undergarment or other clothing worn by the wearer, the absorbent article 10 may catch on the undergarment or other clothing, which can result in the absorbent article 10 being prematurely and undesirably removed from the wearer or may cause the absorbent article 10 to be shifted from its desired placement against the body of a wearer. In order to achieve the desired coefficient of friction of the backsheet layer 44, the materials utilized to form the backsheet layer 44 can be selected such that the garment facing surface of the backsheet layer 44 will inherently have the desired coefficient of friction. Alternatively, the garment facing surface of the backsheet layer 44 can be treated with a coating composition, such as a polytetrafluoroethylene containing coating, a silicone containing coating, or other similar coating have low coefficient of friction properties. Alternatively, the backsheet layer 44 can be made from a laminate of materials such that the material selected for the garment facing surface of the backsheet layer 44 can have the desired coefficient of friction such that the garment facing surface of the backsheet layer 44 can move freely against the undergarment or other clothing worn by the wearer.

Body Adhesive:

A body adhesive 90 is positioned on a portion of the body facing surface 42 of the topsheet layer 40. The body adhesive 90 contacts the skin and hair, if present, in the vulva region and possibly the pubic region and/or the perinea region of the wearer's body, thereby supporting and holding the absorbent article 10 against the body of the wearer during use. The body adhesive 90 can be applied to a portion of the body facing surface 42 of the topsheet layer 40 using any known process including inkjet printing, screen printing, or extruding the body adhesive 90 from one or more nozzles, slot coating, and the like.

Generally, any pressure sensitive adhesive known to those skilled in the art may be used, provided that the pressure sensitive adhesive is not a known irritant to human skin or that the adhesive is so aggressive that it causes pain to the wearer when the absorbent article 10 is removed from the skin. It is also desirable that the adhesive is selected such that the adhesive does not leave a substantial amount of residue on the skin of the wearer, when the absorbent article 10 is removed from the skin. Suitable body adhesive 90 are disclosed in U.S. Pat. No. 6,213,993 to Zacharias et al., and U.S. Pat. No. 6,620,143 to Zacharias et al., the entire disclosure of each is incorporated herein by reference and made a part hereof. Other known body adhesives are disclosed in U.S. Pat. No. 5,618,281 to Batrabet et al., the entire disclosure of which is incorporated herein by reference and made a part hereof. Other known body adhesives, such as those disclosed in U.S. Pat. No. 6,316,524 to Corzani et al., which is hereby incorporated in its entirety, may also be used. Additional examples of pressure sensitive adhesives suitable for use as a body adhesive 90 include hydrogels, hydrocolloids, acrylics based adhesives, and rubber based adhesives, such as Kraton based adhesives.

The body adhesive 90 can be positioned on the body facing surface 42 of the topsheet layer 40 in an open pattern. By "open pattern" is meant that the adhesive 90 can have an intermittent or discontinuous pattern that does not completely encircle the absorbent system 90. For example, there may be breaks in the body adhesive 90 at various portions of the body facing surface 42 of the topsheet layer 40. An example of an "open" pattern of a body adhesive 90 would be to have individual beads of adhesive applied in a discontinuous fashion. In various embodiments, the body adhesive 90 can be positioned on the body facing surface 42 of the topsheet layer 40 in a closed pattern. By "closed pattern" is meant that the adhesive 90 would completely encircle the absorbent system 50 of the absorbent article 10. For example, the pattern of the body adhesive 90 would completely surround the absorbent system 50. A closed pattern can be advantageous as the body adhesive 90 can completely form a seal with the body of the wearer which can assist in preventing leaks from the absorbent article 10. In such embodiments, the body adhesive 90 can form a dam, which may prevent leaks from the entire perimeter of the absorbent article 10. An open pattern can be advantageous as it can allow the absorbent article 10 to flex into the gluteal cleft to provide a close to the body fit of the absorbent article 10. An open pattern can also allow for the absorbent article 10 to flex and twist with the movements of the wearer of the absorbent article 10 without detaching and re-attaching.

Figure 3A:
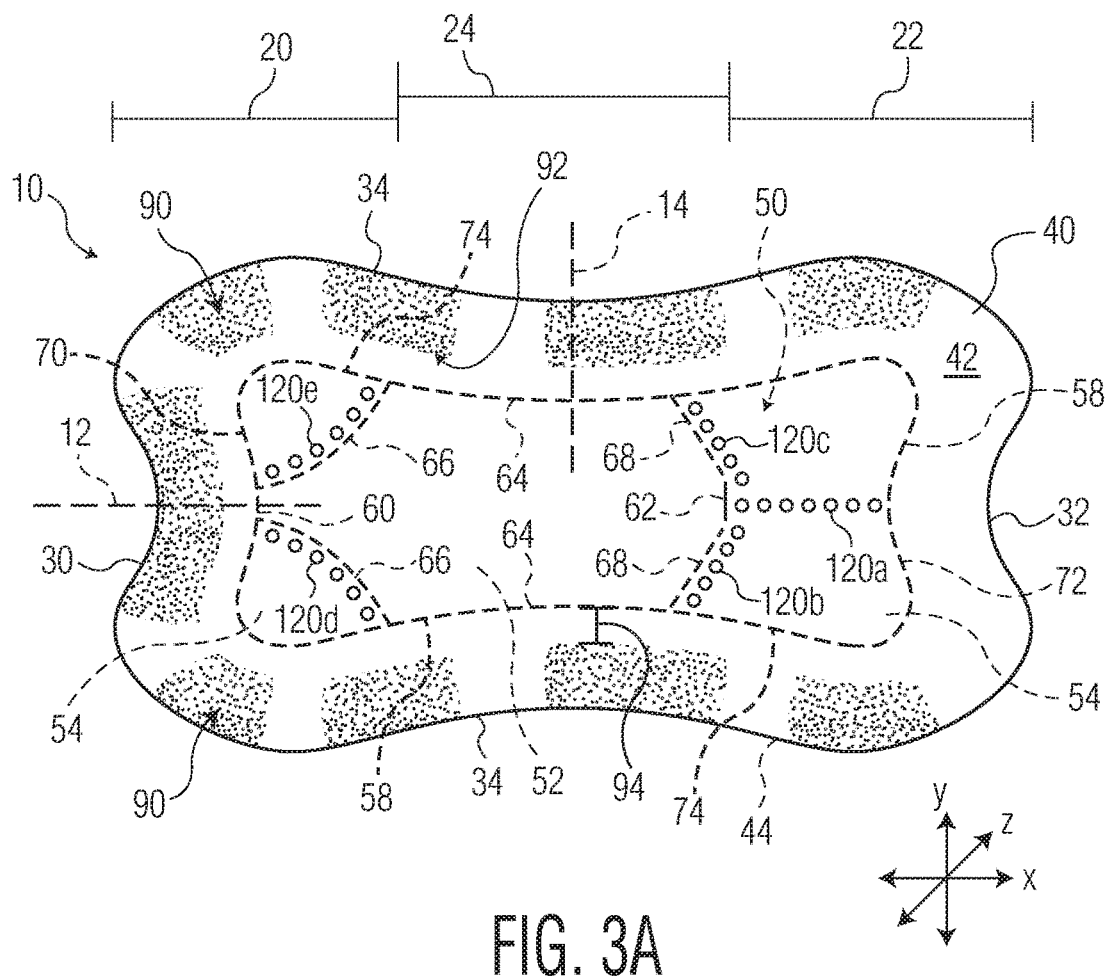
FIG. 3A is a top view of an exemplary embodiment of an absorbent article.
Figure 3B:
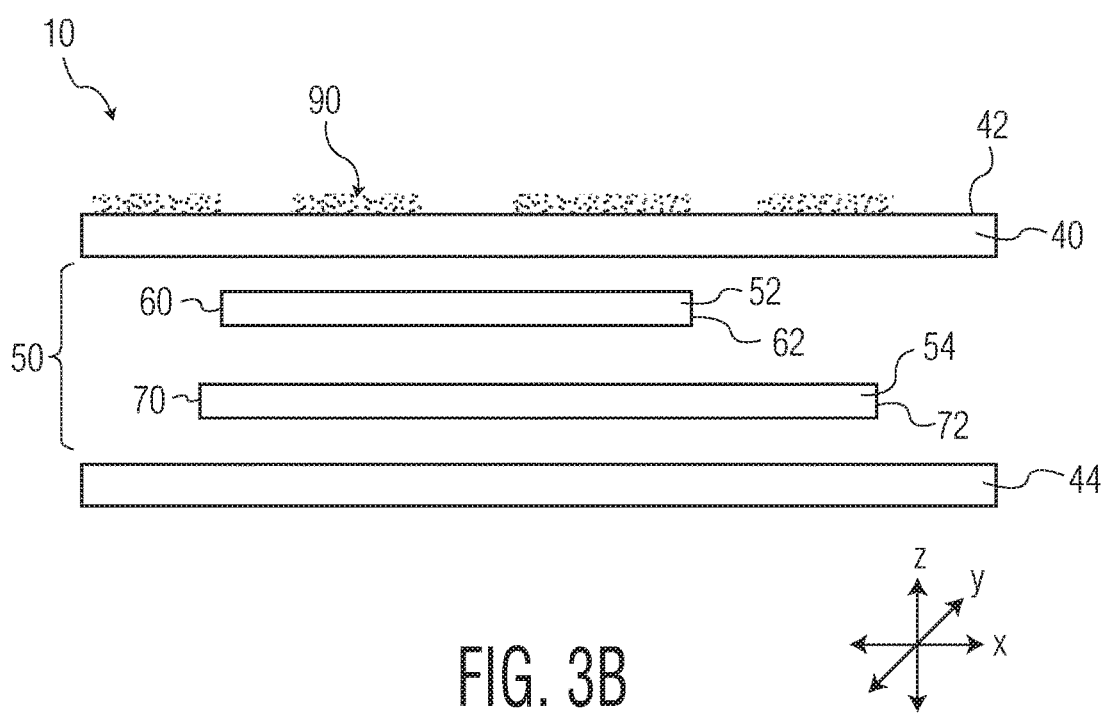
FIG. 3B is an exploded side view of the absorbent article of FIG. 3A.

The body adhesive 90 may be placed on the body facing surface 42 of the topsheet layer 40 between the perimeter edge 58 of the absorbent system 50 and the perimeter edge of the absorbent article 10 such that the body adhesive 90 does not overlay the absorbent system 50. In various embodiments, the body adhesive 90 can be provided in a pattern of small discrete dots so as to leave numerous areas free of adhesive. In various embodiments, the body adhesive 90 can be applied as a continuous bead, or may be applied as a series of semi-continuous beads. For example, referring to FIGS. 1A, 2A, and 4A, the body adhesive 90 can be applied to the body facing surface 42 of the topsheet layer 40 in an open pattern as a generally continuous application of body adhesive 90. The body adhesive can be considered to be an open pattern in such embodiments as a portion of the posterior region 22 of the absorbent article 10 does not have a body adhesive 90 positioned on the body facing surface 42 of the topsheet layer 40. Referring to FIG. 3A, the body adhesive 90 can be applied to the body facing surface 42 of the topsheet layer 40 in a series of semi-continuous beads. Other suitable patterns may be selected for applying the body adhesive 90 to the body facing surface 42 of the topsheet layer 40. For example, adhesive patterns can be oval, swirls, various linear or non-linear arrays of body adhesive 90 longitudinally, and/or transversely oriented and reticulated webs having unobstructed interstices between the adhesive fibers or combinations thereof. The weights of the body adhesive 90 can be less than about 200 grams per square meter ($g/m^2$). In various embodiments, the weight of the body adhesive 90 is at least about 20 $g/m^2$. In various embodiments, the body adhesive 90 can be applied in an amount from about 100 $g/m^2$ to about 200 $g/m^2$. If the basis weight is too high, the weight of the body adhesive will be too heavy and the absorbent article 10 will not be comfortable for the wearer to wearer. If the basis weight of the body adhesive 90 is too low, there may be insufficient adhesion of the absorbent article 10 to the body of the wearer. In various embodiments, the body adhesive 90 can be applied in a manner that is symmetrical about the longitudinal axis 12. This symmetrical pattern can provide the wearer of the absorbent article 10 with a balanced feel when wearing the absorbent article 10.

The body adhesive 90 can have an interior perimeter 92 which is the portion of the body adhesive 90 closest to the absorbent system 50 without coming into a configuration such that it will overlay the absorbent system 50. The interior perimeter 92 of the body adhesive 90 can be separated from the absorbent system 50 by the topsheet layer 40 and can be positioned a spatial distance 94 from the perimeter edge 58 of the absorbent system 50 from about 2, 3, 4 or 5 mm to about 6, 7, 8, 9, or 10 mm. In various embodiments, the spatial distance 94 between the interior perimeter 92 of the body adhesive 90 and the perimeter edge 58 of the absorbent system 50 can be uniform. In various embodiments, the spatial distance 94 between the interior perimeter 92 of the body adhesive 90 and the perimeter edge 58 of the absorbent system 50 can be non-uniform. In various embodiments, a transition from one portion of the body adhesive 90 to another portion of the body adhesive 90 can be an abrupt transition. In various embodiments, a transition from one portion of the body adhesive 90 to another portion of the body adhesive 90 can be a gradual transition. Such a spatial distance 94 between the interior perimeter 92 of the body adhesive 90 and the perimeter edge 58 of the absorbent system 50 can allow for movement of the absorbent article 10 as the wearer moves her body. The spatial distance 94 can isolate the absorbent system 50 of the absorbent article 10 such that when the wearer of the absorbent article 10 moves her body and/or legs, the absorbent system 50 is not impacted by such movement of the wearer. If the body adhesive 90 were not separated by a spatial distance 94 from the absorbent system 50, the movement of the wearer could cause the body adhesive to pull and twist the absorbent system 50 which can lead to movement of the absorbent system 50 out of proper placement for capturing body exudate as well as pulling against sensitive skin of the wearer. Such a spatial distance 94 can also allow for improved adhesion of the absorbent article 10 to the wearer's body. Such a spatial distance 94 can prevent the body adhesive 90 from detaching and re-attaching to the body of the wearer during movement of the wearer. As described herein, the absorbent system 50 can have a height in the depth direction (Z) of the absorbent article 10 and if the interior perimeter 92 of the body adhesive 90 were to be positioned immediately adjacent to the perimeter edge 58 of the absorbent assembly 50 the absorbent article 10 the body adhesive 90 may not adhere to the body of the wearer as the body adhesive 90 may instead adhere to the topsheet layer 40 itself due to the close proximity of the body adhesive 90 to the absorbent assembly 50. The spatial distance 94 between the interior perimeter 92 of the body adhesive 90 and the perimeter edge 58 of the absorbent assembly 50 can be determined based upon the height in the depth direction (Z) of the absorbent assembly 50. The greater the height in the depth direction (Z) of the absorbent assembly then the greater the spatial distance between the interior perimeter 92 of the body adhesive 90 and the perimeter edge 58 of the absorbent assembly 50.

The body adhesive 90 can extend any distance from the interior perimeter 92 of the body adhesive in a direction towards the perimeter edge of the absorbent article 10 as deemed suitable. In various embodiments, such a distance can be from about 5 or 10 mm to about 15 or 20 mm. In various embodiments, at least a portion of the body adhesive 90 abuts the perimeter edge of the absorbent article 10. In various embodiments, at least a portion of the body adhesive 90 does not abut the perimeter edge of the absorbent article 10.

In various embodiments, at least a portion of the posterior region 22 of the absorbent article 10 can be free of body adhesive 90. In such embodiments, the posterior region 22 of the absorbent article 10 can conform to the body of the wearer, such as, for example, folding into the gluteal cleft, to provide a close to the body fit. In various embodiments, the body adhesive 90 can be positioned on the body facing surface 42 of the topsheet layer 40 in a closed pattern such that the body adhesive 90 completely encircles the absorbent assembly 50 of the absorbent article 10.

Figure 5A:
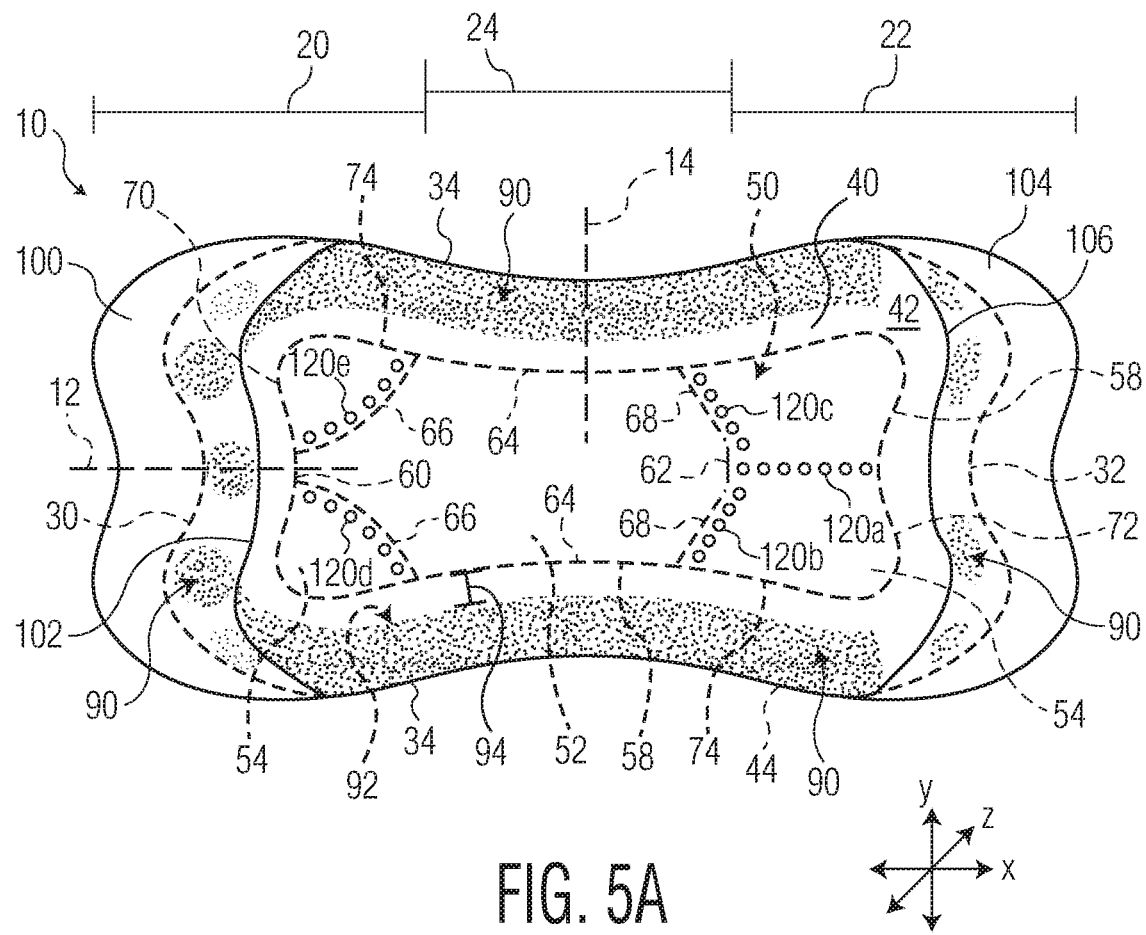
FIG. 5A is a top view of an exemplary embodiment of an absorbent article.
Figure 5B:
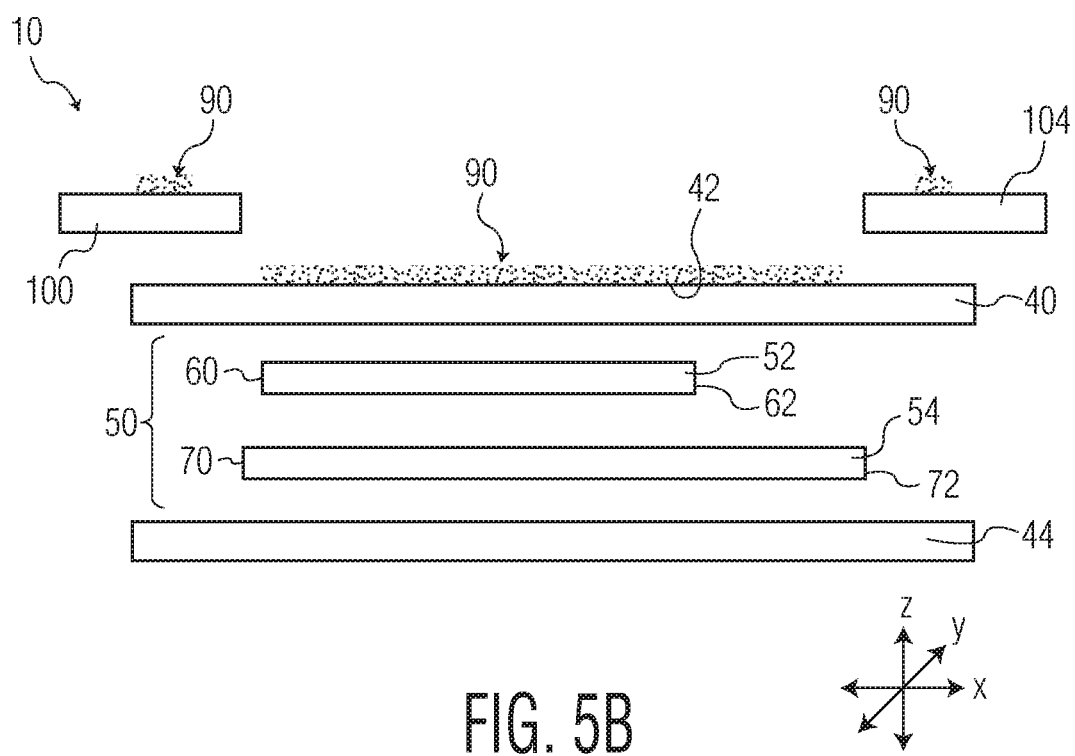
FIG. 5B is an exploded side view of the absorbent article of FIG. 5A.

Secondary Topsheets:

In various embodiments, the absorbent article 10 can have at least one secondary topsheet such as topsheet 100 illustrated in the exemplary embodiment of FIGS. 5A and 5B. In various embodiments, the absorbent article 10 can have two secondary topsheets such as topsheets 100 and 104. In such embodiments, a secondary topsheet(s), 100 and/or 104, can extend beyond a transverse direction end edge, 30 and/or 32, respectively, of the absorbent article 10. In various embodiments, the secondary topsheet(s), 100 and/or 104, can be bonded to the body facing surface 42 of the topsheet layer 40. In various embodiments, the secondary topsheet(s), 100 and/or 104, can be bonded to the backsheet layer 44. In various embodiments, the secondary topsheet(s), 100 and/or 104, can be formed of any of the materials described herein as suitable for the topsheet layer 40. In various embodiments, the secondary topsheet(s), 100 and/or 104, can be formed as a laminate of the materials described herein as suitable for a topsheet layer 40 and backsheet layer 44. The secondary topsheet(s), 100 and/or 104, can provide additional length in the longitudinal direction (X) of the absorbent article 10 and can provide an additional barrier against leakage of body exudates from the absorbent article 10. In various embodiments, the secondary topsheet(s), 100 and/or 104, may also be more pliable than the remainder of the absorbent article 10, such as, for example, by not containing an absorbent assembly, and may demonstrate an improved conformance to the body of the wearer. In various embodiments, the secondary topsheet(s), 100 and/or 104, may each have an interior edge, 102 and 106, respectively. In various embodiments, a body adhesive 90 can be positioned on at least a portion of the secondary topsheet(s), 100 and/or 104, such as, for example, in a position between the interior edge, 102 and 106, of the secondary topsheet(s), 100 and/or 104, respectively, and the transverse direction end edges, 30 and 32, of the absorbent article 10.

Line of Weakness:

In various embodiments, the absorbent article 10 can have one or more line(s) of weakness, generally indicated at 120. The line(s) of weakness can facilitate folding of the absorbent article 10 in various regions to accommodate the body of the wearer and provide close to body fit of the absorbent article 10 to the body of the wearer. Such line(s) of weakness, while facilitating folding of various regions of the absorbent article 10 can prevent folding of various other regions of the absorbent article 10.

Generally, the line(s) of weakness 120 are formed by embossing dashed or dotted lines in the absorbent system 50 and the topsheet layer 40. The size (i.e., length and width) of the individual dashes and dots (broadly, "embossing elements") that define the line(s) of weakness 120 can be varied to alter the characteristics (i.e., resistance to folding) and appearance of the line of weakness. The spacing between the individual dashes and dots can also be varied for the same reasons. The characteristics of the lines of weakness 120 can be altered by varying the size and/or spacing of the dashes/dots along the length of a single line of weakness or by having multiple lines of weakness with different sized or spaced dashes/dots defining the line of weakness. It is understood that the lines of weakness can be formed in other ways besides embossing, including cutting, perforating, bonding, mechanical thinning, or other processes as are known in the art. Additional techniques include, for example, the use of raised elements to impart the desired pattern, such as an embossing pattern, in the layer(s) of the absorbent article 10. For instance, a suitable process may include using thermal bonding wherein the absorbent article 10 is passed through two rolls (e.g., steel, rubber, etc.) where one is engraved with an embossing pattern and the other is flat. One or both rolls may be heated. In addition, thermal and/or ultrasonic bonding techniques may be employed to create the lines of weakness. In various embodiments, a line of weakness 120 can be formed due to the variable height in the absorbent system 50. In various embodiments, the backsheet layer 44 is free from the lines of weakness 120. In various embodiments, the backsheet layer 44 can include the lines of weakness 120.

The lines of weakness 120 can be formed in any suitable pattern to not only create an aesthetically pleasing surface, but also to facilitate folding of the absorbent article 10 and funneling of body exudates towards a desired location in the absorbent article 10. The lines of weakness 120 may also improve the consistency of the fit properties of the absorbent article 10, both before and after receiving body exudates. The lines of weakness 120 may be provided in either a symmetric or asymmetric manner to the absorbent article 10. In various embodiments, a line of weakness 120 can be positioned to be adjacent to the absorbent assembly 50 without penetrating into the absorbent assembly 50.

FIGS. 1A, 2A, 3A, 4A, and 5A provide exemplary illustrations of embodiments of absorbent articles 10 having multiple lines of weakness 120. In various embodiments, a first line of weakness 120a can extend generally along the longitudinal axis 12 of the absorbent article 10 in the posterior region 22. Two second lines of weakness, 120b and 120c, flank the first line of weakness 120a. The second lines of weakness, 120b and 120c, diverge as they extend away from the first line of weakness 120a and generally form a V-shape in the posterior region of the absorbent article 10. The first line of weakness 120a and the second lines of weakness, 120b and 120c, can facilitate folding of the absorbent article 10 during usage of the absorbent article 10 such that the posterior region 22 of the absorbent article 10 is received in the gluteal cleft of the wearer. The gluteal cleft has been found to provide a passageway for body exudates to leak and placement of the posterior region 22 of the absorbent article 10 into the gluteal cleft can block this potential passageway and thereby inhibit leakage of body exudates. The absorbent article 10 can further have third lines of weakness, 120d and 120e, in the anterior region 20 of the absorbent article 10. Such third lines of weakness, 120d and 120e, can diverge away from each other as they extend from the longitudinal axis 12 towards the longitudinal direction side edges of the absorbent assembly 50 and generally form a V-shape in the anterior region 20 of the absorbent article 10. Such third lines of weakness, 120d and 120e, can facilitate folding of the absorbent article 10 to conform to the contours of the wearer's body in the anterior region of the vulva region of the wearer's body. FIG. 6A provides an illustration of an embodiment of an absorbent article 10 having a pair of lines of weakness, 120b and 120c, which diverge and generally form a V-shape in the posterior region 22 of the absorbent article 10.

Notch:

Referring to FIG. 6A, an absorbent article 10 comprising at least one notch 110 is illustrated. The notch 110 can be positioned to extend from the perimeter edge of the absorbent article 10 and in a direction towards the interior of the absorbent article 10. In various embodiments, the notch 110 can extend a depth from the perimeter edge of the absorbent article 10 to the proximity of the interior perimeter 92 of the body adhesive 90. In various embodiments, the notch 110 does not extend beyond the interior perimeter 92 of the body adhesive 90 as this could provide a passageway for leakage of body exudate from the absorbent system 50 of the absorbent article 10. In various embodiments, the absorbent article 10 can have at least 1, 2, 3, or 4 notches 110. The presence of a notch 110 in an absorbent article 10 can provide a location where material forming the absorbent article 10 is absent as well as providing a location where body adhesive 90 is absent. The absence of material forming the absorbent article 10 and the absence of body adhesive 90 due to the presence of a notch 110 can provide a location where the absorbent article 10 can flex and experience stress relief as the wearer moves and as the absorbent article 10 moves with the wearer. A notch 110, therefore, is a discontinuity in the mechanical properties of the absorbent article 10 and a discontinuity in the manner of attachment between the absorbent article 10 and the skin of the wearer. A notch 110 can, therefore, provide for improved comfort to the wearer in the usage of the absorbent article 10. In various embodiments, an absorbent article 10 can have a pair of notches 110 positioned in the posterior region 22 of the absorbent article 10. In various embodiments, an absorbent article 10 can have a pair of notches 110 positioned in the anterior region 20 of the absorbent article 10. A notch 110 can be configured in any shape deemed suitable to provide a flex point within the absorbent article 10. Such shapes can include, for example, triangle, oval, elliptical, square, rectangular, etc. In various embodiments, the exterior perimeter edge of the notch 110 can be arcuate so as to provide a smooth transition between the notch 110 and the perimeter edge of the absorbent article 10.

In the interests of brevity and conciseness, any ranges of values set forth in this disclosure contemplate all values within the range and are to be construed as support for claims reciting any sub-ranges having endpoints which are whole number values within the specified range in question. By way of hypothetical example, a disclosure of a range of from 1 to 5 shall be considered to support claims to any of the following ranges 1 to 5; 1 to 4; 1 to 3; 1 to 2; 2 to 5; 2 to 4; 2 to 3; 3 to 5; 3 to 4; and 4 to 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description are, in relevant part, incorporated herein by reference; the citation of any documents is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

What is claimed is:

1. An absorbent article comprising:
 a. a longitudinal direction and a transverse direction;
 b. an anterior region, a posterior region, and a central region positioned between the anterior region and the posterior region;
 c. a first transverse direction end edge and a second transverse direction end edge opposed to the first transverse direction end edge defining part of an article perimeter edge;
 d. a topsheet layer comprising a body facing surface;
 e. a backsheet layer;
 f. an absorbent system positioned between the topsheet layer and the backsheet layer, the absorbent system comprising an absorbent core and a perimeter edge where the topsheet layer covers the entirety of the absorbent core and extends beyond the perimeter edge of the absorbent core;
 g. a depth direction wherein the absorbent system has a variable height in the depth direction in the longitudinal direction;
 h. a pair of lines of weakness in the posterior region which generally form a V-shape;
 i. a body adhesive positioned on a portion of the body facing surface of the topsheet layer, the body adhesive comprising a continuous adhesive region extending through each of the anterior region, the posterior region, and the central region, the continuous adhesive region comprising an interior perimeter which is separated by a spatial distance from the perimeter edge of the absorbent system such that the entirety of the interior perimeter of the continuous adhesive region is disposed between the absorbent system and the article perimeter edge; and
 j. a notch extending from the perimeter edge of the absorbent article and in a direction towards a longitudinal axis of the absorbent article, the notch being formed in both the topsheet layer and the backsheet layer and not being formed in the absorbent system, wherein the notch does not extend inward beyond the interior perimeter of the continuous adhesive region of the body adhesive.

2. The absorbent article of claim 1 wherein the pair of lines of weakness are formed by embossing lines.

3. The absorbent article of claim 1 wherein the height in the depth direction of the absorbent system in a portion of the anterior region of the absorbent article is greater than the height in the depth direction of the absorbent article in a portion of the posterior region of the absorbent article.

4. The absorbent article of claim 1 wherein the spatial distance separating the interior perimeter of the continuous adhesive region of the body adhesive from the perimeter edge of the absorbent system is from 2 mm to 10 mm.

5. The absorbent article of claim 1 wherein the spatial distance between the interior perimeter of the continuous adhesive region of the body adhesive and the perimeter edge of the absorbent system is uniform.

6. The absorbent article of claim 1 wherein the spatial distance between the interior perimeter of the continuous adhesive region of the body adhesive and the perimeter edge of the absorbent system is non-uniform.

7. The absorbent article of claim 1 wherein a portion of the posterior region of the absorbent article is free from the continuous adhesive region.

8. The absorbent article of claim 1 further comprising a distribution layer.

9. The absorbent article of claim 8 wherein the distribution layer has a length in the longitudinal direction which is longer than a length in the longitudinal direction of the absorbent core.

10. The absorbent article of claim 1 wherein the notch is located in the posterior region of the absorbent article.

11. The absorbent article of claim 1 further comprising a second notch extending from the perimeter edge of the absorbent article and in a direction towards the longitudinal axis of the absorbent article in the anterior region of the absorbent article, the second notch being formed in both the topsheet layer and the backsheet layer.

12. The absorbent article of claim 1 further comprising a secondary topsheet which extends beyond the first and/or second transverse direction end edges.

13. The absorbent article of claim 1 further comprising a second pair of lines of weakness in the anterior region of the absorbent article which generally form a V-shape.

14. The absorbent article of claim 1 further comprising a fluid intake layer.

15. The absorbent article of claim 14 wherein the fluid intake layer comprises an opening.

16. The absorbent article of claim 1, wherein the continuous adhesive region extends to the article perimeter edge.

17. An absorbent article comprising:
 a. a longitudinal direction and a transverse direction;
 b. an anterior region, a posterior region, and a central region positioned between the anterior region and the posterior region;
 c. a first transverse direction end edge and a second transverse direction end edge opposed to the first transverse direction end edge defining part of an article perimeter edge;
 d. a topsheet layer comprising a body facing surface;
 e. a backsheet layer;
 f. an absorbent system positioned between the topsheet layer and the backsheet layer, the absorbent system comprising an absorbent core and a perimeter edge where the topsheet layer covers the entirety of the absorbent core and extends beyond the perimeter edge of the absorbent core;
 g. a depth direction wherein the absorbent system has a variable height in the depth direction in the longitudinal direction;
 h. a pair of lines of weakness in the posterior region which generally form a V-shape;
 i. a body adhesive positioned on a portion of the body facing surface of the topsheet layer, the body adhesive comprising a continuous adhesive region extending through each of the anterior region, the posterior region, and the central region, the continuous adhesive region comprising an interior perimeter which is separated by a spatial distance from the perimeter edge of the absorbent system such that the entirety of the interior perimeter of the continuous adhesive region is disposed between the absorbent system and the article perimeter edge; and j. a secondary topsheet which extends beyond the first and/or second transverse direction end edges, wherein the secondary topsheet is connected to the topsheet layer but does not overlap the absorbent core, and wherein the secondary topsheet further comprises body adhesive disposed on the secondary topsheet.

18. An absorbent article comprising:
a. a longitudinal direction and a transverse direction;
b. an anterior region, a posterior region, and a central region positioned between the anterior region and the posterior region;
c. a first transverse direction end edge and a second transverse direction end edge opposed to the first transverse direction end edge defining part of an article perimeter edge;
d. a topsheet layer comprising a body facing surface;
e. a backsheet layer;
f. an absorbent system positioned between the topsheet layer and the backsheet layer, the absorbent system comprising an absorbent core and a perimeter edge where the topsheet layer covers the entirety of the absorbent core and extends beyond the perimeter edge of the absorbent core;
g. a depth direction wherein the absorbent system has a variable height in the depth direction in the longitudinal direction;
h. a pair of lines of weakness in the posterior region which generally form a V-shape; and
i. a body adhesive positioned on a portion of the body facing surface of the topsheet layer, the body adhesive comprising a continuous adhesive region extending through each of the anterior region, the posterior region, and the central region, the continuous adhesive region comprising an interior perimeter which is separated by a spatial distance from the perimeter edge of the absorbent system such that the entirety of the interior perimeter of the continuous adhesive region is disposed between the absorbent system and the article perimeter edge, wherein the spatial distance between the interior perimeter of the continuous adhesive region of the body adhesive and the perimeter edge of the absorbent system is determined based upon the height in the depth direction of the absorbent system, wherein the greater the height in the depth direction of the absorbent system then the greater the spatial distance between the interior perimeter of the continuous adhesive region of the body adhesive of the topsheet and the perimeter edge of the absorbent system.

* * * * *